US007781397B2

(12) United States Patent
Stern et al.

(10) Patent No.: US 7,781,397 B2
(45) Date of Patent: *Aug. 24, 2010

(54) HUMAN PLASMA HYALURONIDASE

(75) Inventors: Robert Stern, San Francisco, CA (US); Gregory I. Frost, San Francisco, CA (US); Anthony Csoka, San Francisco, CA (US); Tim M. Wong, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/538,246

(22) Filed: Oct. 3, 2006

(65) Prior Publication Data
US 2007/0134228 A1 Jun. 14, 2007

Related U.S. Application Data

(63) Continuation of application No. 09/795,914, filed on Feb. 27, 2001, now Pat. No. 7,148,201, which is a continuation of application No. 08/916,935, filed on Aug. 21, 1997, now Pat. No. 6,193,963, which is a continuation-in-part of application No. 08/733,360, filed on Oct. 17, 1996, now Pat. No. 6,103,525.

(51) Int. Cl.
A01N 37/18 (2006.01)
(52) U.S. Cl. ............................................... 514/2; 514/8
(58) Field of Classification Search ....................... None
See application file for complete search history.

(56) References Cited

U.S. PATENT DOCUMENTS

| 3,945,889 A | 3/1976 | Mima et al. |
| 5,427,779 A | 6/1995 | Elsner et al. |

FOREIGN PATENT DOCUMENTS

| WO | WO 88/02261 | 4/1988 |
| WO | WO 89/05329 | 6/1989 |
| WO | WO 96/03497 | 2/1996 |
| WO | WO 96/31596 | 10/1996 |

OTHER PUBLICATIONS

Bowie et al (Science, 1990, 257:1306-1310).*
Lazar et al (Molecular and Cellular Biology, 1988, 8:1247-1252).*
Burgess et al ( J of Cell Bio. 111:2129-2138, 1990).*
Triggs-Raine et al (PNAS, 1999, 96:6296-6300).*
Afify et al., (1993) "Purification and Characterization of Human Serum Hyaluronidase" Arch. Biochem. Biophys. 305 (2):434-441.
Balicki et al. (2002) "Gene Therapy of Human Disease" Medicine vol. 81, pp. 69-86.
Baumgartner et al., (1988) "Phase I Study in Chemoresistant Locoregional Malignant Disease with Hyaluronidase" Reg. Cancer Treat. 1:55-58.
Beckenlehner et al., (1992) "Hyaluronidase Enhances the Activity of Adriamycin in Breast Cancer Models in Vitro and in Vivo" J. Cancer Res. Oncol. 118:591-596.
Bollet et al. (1963) "The Presence of Hyaluronidase in Various Mammalian Tissues", J. Biol. Chem., vol. 238, No. 11, pp. 3522-3527.
Bonner et al., (1966) "Colorimetric Method for Determination of Serum Hyaluronidase Activity" Clinica Chimica Acta 13:746-752.
Bordier, (1981) "Phase Separation of Integral Membrane Proteins in Triton X-114 Solution" J. Biol. Chem. 256(4):1604-1607.
Bowness et al. (1968) "Chromatographic Distinction Between Hyaluronidases from Human Serum and Ovine Testes", Jan. 8, 1968, vol. 151, No. 1, pp. 288-290.
Cashman et al., (1969) "The Hyaluronidase of Rat Skin" Arch. Biochem. Biophys. 135:387-395.
Chang N.S. (1998) "Transforming Growth Factor-beta Protection of Cancer Cells Against Tumor Necrosis Factor Cytotoxicity is counteracted by Hyaluronidase" (1998) INt. J. Mol. Med., vol. 2, No. g, pp. 653-659.
Csoka et al. (1997) "Hyaluronidases in Tissue Invasion" Invasion and Metastasis vol. 17, No. 6, pp. 297-311.
Czejka et al., (1990) "Influence o hyaluronidase on the blood plasma levels of 5-fluorouracil in patients," Pharmazie 45:H.9.
De Maeyer et al., (1992) "The Growth Rate of Two Transplantable Murine Tumors, 3LL Lung Carcinoma and B16F10 Melanoma, Is Influenced by Hyal-I, A Locus Determining Hyaluronidase Levels and Polymorphism" Int. J. Cancer 51:657-660.
De Salegui et al., (1967) "A Comparison of Serum and Testicular Hyaluronidase" Arch. Biochem. Biophys. 121:548-554.
De Salegui et al. (1967) "The existence of an Acid-Active Hyaluronidase in Serum", Abstract No. 29394, Chemical Abstracts, vol. 67, No. 7, Issued 1967, p. 2766.
De Salegui et al. (1967) Arch. Biochem Biophys., vol. 120, No. 1, pp. 60-67.
Delpech et al., (1987) "An Indirect Enzymoimmunology Assay for Hyaluronidase" J. Immunol. Methods 104:223-229.

(Continued)

Primary Examiner—Misook Yu
Assistant Examiner—Mark Halvorson
(74) Attorney, Agent, or Firm—Paula A. Borden; Bozicevic, Field & Francis LLP

(57) ABSTRACT

The invention is based on the discovery of methods for purification of an acid active hyaluronidase found in human plasma (hpHAse), including both biochemical and immunoaffinity purification methods. The method of immunoaffinity purification of the invention is based on the discovery of a method for identifying antibodies that specifically bind native hpHAse (anti-native hpHAse antibodies), and anti-native hpHAse antibodies identified by this screening method. The invention also features an assay for sensitive detection of HAse activity using biotinylated hyaluronic acid (bHA). Purification and characterization of hpHAse lead to the inventors' additional discovery that hpHAse is encoded by the LuCa-1 gene, which gene is present in the human chromosome at 3p21.3, a region associated with tumor suppression. The invention additionally features methods of treating tumor-bearing patients by administration of hpHAse and/or transformation of cells with hpHAse-encoding DNA.

29 Claims, 9 Drawing Sheets

OTHER PUBLICATIONS

Doctor et al., (1983) "Isolation and Properties of a New Anticoagulant Protein from Commercial Bovine Testicular Hyaluronidase" Thrombosis Res. 30:565-571.
Dorfman et al., (1948) "A Turbidimetric Method for the Assay of Hyalaronidase" J. Biol. Chem. 172:367-375.
Eck, S. L. et al (1996) "Gene-Bases thereapy" in The Pharmacological Basis of therapeutics, Goodman & Gilman's, McGraq-Hill, Ninth Edition, pp. 77-101.
Fenger et al (1982) "Purification of Human Serum Hyaluronidase Using Chromatofocusing." (J. Chromatogr. 240:173-179).
Fiszer-Szafarz et al. (1984) "Hyaluronidase Polymorphism Detected by Polyacrylamide Gel Electrophoresis. Application to Hyaluronidases from Bacteria, Slime Molds, Bee and Snake Venoms, Bovine Testes, Rat Liver Lysosomes and Human Serum", Anal. Biochem., vol. 143, pp. 76-81.
Fiszer-Szafarz et al., (1989) "Hyal-I, a Locus Determining Serum Hyaluronidase Polymorphism, in Chromosome 9 in Mice" Somat. Cell. Mol. Genet. 15:79-83.
Fiszer-Szafarz et al., (1995) "Hyaluronidase in Human Somatic Tissues and Urine: Polymorphism and the Activity in Diseases," Acta Biochim Pol. 42:31-3.
Frost et al. (1997) "Purification, Cloning and Expression of Human Plasma Hyaluronidase", Biochem Blophys. Res. Comm., vol. 236, No. 1, pp. 10-15.
Gabizon (1995) "Stealth Liposomes and Cancer Targeting: A Realistic Compromise in Drug Delivery." (J. Liposome Res., 5:704-710).
Genbank accession No. U03056, deposited Nov. 1, 1993.
Gregoriadis et al. (1993)"Liposomes in drug delivery. Clinical, diagnostic and ophthalmic potential." (Drugs, 45:15-28).
Guntenhoner et al., (1992) "A Substrate-Gel Assay for Hyaluronidase Activity" Matrix 12:388-396.
Harrison et al., (1988) "Multiple Forms of Ram and Bull Sperm Hyaluronidase Revealed by Using Monoclonal Antibodies" J. Reprod Fertil. 82:777-785.
Hegi et al., (1994) "Allelotype Analysis of Mouse lung Carcinomas Reveals Frequent Allelic Losses on Chromosome 4 and an Association between Allelic Imbalances on Chromosome 6 and K-ras Activation," Cancer Research 54, pp. 6257-6264.
Horn et al., (1985) "Intravesical Chemotherapy of Superficial Bladder Tumors in a Controlled Trial with Cis-Platinum Versus Cis-Platinum Plus Hyaluronidase" J. Surg. Oncol. 28:304-307.
Johnstone et al. (1987)(Immunochemistry in Practice, Blackwell Scientific Publications, Oxford, pp. 30-31).
Kimata et al., (1983) "Increased Synthesis of Hyaluronic Acid by Mouse Mammary Carcinoma Cell Variants with High Metastatic Potential" Cancer Res. 43:1347-1354.
Kohno et al., (1994) "Effects of Hyaluronidase on Doxorubicin Penetration Into Squamous Carcinoma Multicellular Tumor Spheroids and Its Cell Lethality" J. Cancer Res. Clin. Oncol. 120:293-297.
Kolarova et al., (1970) "Host-Tumour Relationship XXIX. Hyaluronidase Activity and Seromucoid Concentration in Blood Serum of Patients with Cancer" Neoplasma 17:641-648.
Komender et al., (1973) "Isolation of Hyaluronidase from Kidney Extract," Bull Acad. Pol. Sci. (Biol.) 21:637-41.
Kreil, (1995) "Hyaluronidases—A Group of Neglected Enzymes" Protein Sci. 4:1666-1669.
Lepperdinger, G. et al. (2001) "Hyal2—Less Active, But Nore Versatile?" Matrix Biol. vol. 20, pp. 509-514.
Levvy et al., (1966) "Mammalian Glycosidases and Their Inhibition by Aldonolactones" Method Enzymol. 8:571-584.
Lin Ji et al.(2002)"Expresions of Several Genes in the Human Chromosome 3p21.3 Homozygous Deletion Region by an Adenovirus Vector Results in Tumor Suppressor Activities in Vitro" Cancer Res. 62 pgs. 2715-2720.
Lien et al., (1990) "Collagen, Proteoglycan and Hyaluronidase Activity in Cultures from Normal and Scoliotic Chicken Fibroblasts" Biochim. Biophys. Acta. 1034:318-325.
Liu et al., (1996) "Expression of Hyaluronidase by Tumor Cells Induces Angiogenesis In Vivo" Proc. Natl. Acad. Sci. USA 93 (15):7832-7837.

Margolis et al., (1972) "The Hyaluronidase of Brain," J. Neutrochem. 19:2325-32.
Natowicz et al., (1996) "Clinical and Biochemical Manifestations of Hyaluronidase Deficiency" N. Engl. J. Med. 335 (14)1029-1033.
Natowicz, et al., (1996) "Human Serum Hyaluronidase: Characterization of a Clinical Assay," Clinical. Chimica. Acta., 245:1-6.
Nishikawa, M. et al. (2001) "Nonviral Vectors in the New Millennium: Delivery Barrier in Gene Transfer" Hum Gene Ther vol. 12, pp. 861-870.
Northrup et al., (1973) "Development of the Hyaluronidase Activity Assay As A Cancer Screening Test" Clin. Biochem. 6:220-228.
Orkin, S.H. et al. (1995) "Report and Recommendations of the Panel to Assess the NIH Investment in Research on Gene Therapy".
Palowski et al., (1981) "The Effects of Hyaluronidase Upon Tumor Formation in BALB/c Mice Irradiated with Ultraviolet Light" Carcinogenesis (Proceedings of the 17th Annual Meeting of the American Society of Clinical Oncology), Washington, D.C., 22:105,(abstract 415).
Pawlowski et al., (1979) "Effects of Hyalurodinase Upon Tumor Formation in BALB c Mice Painted with 7,12-Dimethylbenz-(α)Anthracene" Int. J. Cancer 23:105-109.
Reissig et al., (1955) "A Modified Colorimetric Method for the Estimation of N-Acetylamino Sugars" J. Biol. Chem. 217:959-966.
Rosenberg, Y et al. (2001) "Alternative Gene Delivery" S.T.P. Pharma Sci, vol. 11, pp. 21-30.
Ruggiero et al., (1987) "Hyaluronidase Activity of Rabbit Skin Wound Granulation Tissue Fibroblasts" J. Dent. Res. 66(7):1283-1287.
Scheithauer et al., (1988) "In Vitro Evaluation of the Anticancer Drug Modulatory Effect of Hyaluronidase in Human Gastrointestinal Cell Lines" Anticancer Res. 8:391-396.
Schuller et al., (1991) "Pharmacokinetics of Intrahepatic 5-Fluorouracil ± Preinjected Hyaluronidase (Neopermease, N)" Proc. Amer. Assoc. Cancer Res. 32:173, (Abstract No. 1034).
Stern et al., (1992) "An Elisa-Like Assay for Hyaluronidase and Hyaluronidase Inhibitors" Matrix 12:397-403.
Thet et al., (1983) "Changes in Lung Hyaluronidase Activity Associated with Lung Growth, Injury and Repair" Biochem. Biophys. Res. Commun. 117:71-77.
Underhili, (1991) "CD44: The Hyaluronan Receptor" J. Cell Science 103:293-298.
Van Den Berg at al., (1995) "Exogenous Glycosyl Phosphatidylinositol-anchored CD59 Associates with Kinases in Membrane Clusters on U937 Cells and Becomes $Ca^{2+}$-signaling Competent" J. Cell Biology 131(3):669-677.
Verma et al. (1997) "Gene Therapy-promises, Problems and Prospects" Nature vol. 389, pp. 239-242.
Wolf et al., (1982) "The Serum Kinetics of Bovine Testicular Hyaluronidase in Dogs, Rats and Humans" J. Pharmacol. Exper. Therap. 222(2):331-337.
Zanker et al., (1986) "Induction of Response in Previous Chemotherapy Resistant Patients by Hyaluronidase" Proc. Amer. Assoc. Cancer Res. 27:390 (Abstract 1550).
Gmachl and Kreil. Bee venom hyaluronidase is homologous to a membrane protein of mammalian sperm.Gmachl M, Kreil G. Proc Natl Acad Sci U S A. Apr. 15, 1993;90(8):3569-73.
Kreil. Hyaluronidases—a group of neglected enzymes. Protein Sci. Sep. 1995;4(9):1666-9.
Lathrop, et al. cDNA cloning reveals the molecular structure of a sperm surface protein, PH-20, involved in sperm-egg adhesion and the wide distribution of its gene among mammals. J Cell Biol. Dec. 1990;111(6 Pt 2):2939-49.
Lin, et al. Molecular cloning of the human and monkey sperm surface protein PH-20. Proc Natl Acad Sci U S A. Nov. 1, 1993;90(21):10071-5.
Lu, et al. Sequence identity and antigenic cross-reactivity of white face hornet venom allergen, also a hyaluronidase, with other proteins. J Biol Chem. Mar. 3, 1995;270(9):4457-65.
Arming et al. In vitro mutagenesis of PH-20 hyaluronidase from human sperm. (1997) Eur. J. Biochem. 247, pp. 810-814.

* cited by examiner

FIG. 5

SEQUENCE LISTING

<160> NUMBER OF SEQ ID NOS: 11

<210> SEQ ID NO 1
<211> LENGTH: 435
<212> TYPE: PRT
<213> ORGANISM: Homo sapiens

<400> SEQUENCE: 1

```
Met Ala Gly His Leu Leu Pro Ile Cys Ala Leu Phe Leu Thr Leu Leu
 1               5                  10                  15

Asp Met Ala Gln Gly Phe Arg Gly Pro Leu Leu Pro Asn Arg Pro Phe
                20                  25                  30

Thr Thr Val Trp Asn Ala Asn Thr Gln Trp Cys Leu Glu Arg His Gly
            35                  40                  45

Val Asp Val Asp Val Ser Val Phe Asp Val Val Ala Asn Pro Gly Gln
        50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
               100                 105                 110

Ile Leu Ala Ala Ile Pro Ala Pro Asp Phe Ser Gly Leu Ala Val Ile
           115                 120                 125

Asp Trp Glu Ala Trp Arg Pro Arg Trp Ala Phe Asn Trp Asp Thr Lys
       130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Gly Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
```

-continued

```
                275                 280                 285
Ile Phe Tyr Asp Thr Thr Asn His Phe Leu Pro Leu Asp Glu Leu Glu
    290                 295                 300
His Ser Leu Gly Glu Ser Ala Ala Gln Gly Ala Ala Gly Val Val Leu
305                 310                 315                 320
Trp Val Ser Trp Glu Asn Thr Arg Thr Lys Glu Ser Cys Gln Ala Ile
                325                 330                 335
Lys Glu Tyr Met Asp Thr Thr Leu Gly Pro Phe Ile Leu Asn Val Thr
            340                 345                 350
Ser Gly Ala Leu Leu Cys Ser Gln Ala Leu Cys Ser Gly His Gly Arg
        355                 360                 365
Cys Val Arg Arg Thr Ser His Pro Lys Ala Leu Leu Leu Asn Pro
370                 375                 380
Ala Ser Phe Ser Ile Gln Leu Thr Pro Gly Gly Pro Leu Ser Leu
385                 390                 395                 400
Arg Gly Ala Leu Ser Leu Glu Asp Gln Ala Gln Met Ala Val Glu Phe
                405                 410                 415
Lys Cys Arg Cys Tyr Pro Gly Trp Gln Ala Pro Trp Cys Glu Arg Lys
            420                 425                 430
Ser Met Trp
        435

<210> SEQ ID NO 2
<211> LENGTH: 21
<212> TYPE: PRT
<213> ORGANISM: Homo sapiens

<400> SEQUENCE: 2

Met Ala Gly His Leu Leu Pro Ile Cys Ala Leu Phe Leu Thr Leu Leu
  1               5                  10                  15
Asp Met Ala Gln Gly
            20

<210> SEQ ID NO 3
<211> LENGTH: 435
<212> TYPE: PRT
<213> ORGANISM: Homo sapiens

<400> SEQUENCE: 3

Met Ala Gly His Leu Leu Pro Ile Cys Ala Leu Phe Leu Thr Leu Leu
  1               5                  10                  15
Asp Met Ala Gln Gly Phe Arg Gly Pro Leu Val Pro Asn Arg Pro Phe
                20                  25                  30
Thr Thr Val Trp Asn Ala Asn Thr Gln Trp Cys Leu Glu Arg His Gly
            35                  40                  45
Val Asp Val Asp Val Ser Val Phe Asp Val Val Ala Asn Pro Gly Gln
    50                  55                  60
Thr Phe Arg Gly Pro Asp Met Thr Ile Phe Tyr Ser Ser Gln Leu Gly
65                  70                  75                  80
Thr Tyr Pro Tyr Tyr Thr Pro Thr Gly Glu Pro Val Phe Gly Gly Leu
                85                  90                  95
Pro Gln Asn Ala Ser Leu Ile Ala His Leu Ala Arg Thr Phe Gln Asp
                100                 105                 110
Ile Leu Ala Ala Ile Pro Ala Pro Asp Phe Ser Gly Leu Ala Val Ile
            115                 120                 125
Asp Trp Glu Ala Trp Arg Pro Arg Trp Ala Phe Asn Trp Asp Thr Lys
```

```
                130             135             140
Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Gly Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
                260                 265                 270

Ala Val Ala Ala Gly Asp Pro Asn Leu Pro Val Leu Pro Tyr Val Gln
            275                 280                 285

Ile Phe Tyr Asp Thr Thr Asn His Phe Leu Pro Leu Asp Glu Leu Glu
        290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
                340                 345                 350

Ser Gly Ala Leu Leu Cys Ser Gln Ala Leu Cys Ser Gly His Gly Arg
            355                 360                 365

Cys Val Arg Arg Thr Ser His Pro Lys Ala Leu Leu Leu Leu Asn Pro
        370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
                420                 425                 430

Ser Met Trp
        435

<210> SEQ ID NO 4
<211> LENGTH: 2517
<212> TYPE: DNA
<213> ORGANISM: Homo sapiens

<400> SEQUENCE: 4
ttcctccagg agtctctggt gcagctgggg tggaatctgg ccaggccctg cttaggcccc      60
catcctgggg tcaggaaatt tggaggataa ggcccttcag ccccaaggtc agcagggacg     120
agcgggcaga ctggcgggtg tacaggaggg ctgggttgac ctgtccttgg tcactgaggc     180
cattggatct tcctccagtg gctgccagga tttctggtgg aagagacagg aaggcctccc     240 cccttggtc gggtcagcct gggggctgag ggcctggctg tcagccactc ttcccagaac     300
atatgtcatg gcctcagtgg ctcatgggga agcaggggtg ggcagcctta ggctagagca     360
```

-continued

```
agtcctgtgg gagatggcag aggcctggtc tgagaggcaa ctcggatgtg ccctccagtg    420
gccatgctcc cctccatgcg tctcccctgc cctcctggag ccctgcaggt caatgtttaa    480
cagaaaccag agcagcggtg gattaatgcg caagggctca gccccccagc cctgagcagt    540
gggggaatcg gagactttgc aacctgttct cagctctgcc tcccctgggc aggttgtcct    600
cgaccagtcc cgtgccatgg caggccacct gcttcccatc tgcgccctct tcctgacctt    660
actcgatatg gcccaaggct ttaggggccc cttggtaccc aaccggccct tcaccaccgt    720
ctggaatgca acacccagt ggtgcctgga gaggcacggt gtggacgtgg atgtcagtgt    780
cttcgatgtg gtagccaacc cagggcagac cttccgcggc cctgacatga caattttcta    840
tagctcccag ctgggcacct acccctacta cacgcccact ggggagcctg tgtttggtgg    900
tctgccccag aatgccagcc tgattgccca cctggcccgc acattccagg acatcctggc    960
tgccataccc gctcctgact tctcagggct ggcagtcatc gactgggagg catggcgccc   1020
acgctgggcc ttcaactggg acaccaagga catttaccgg cagcgctcac gggcactggt   1080
acaggcacag caccctgatt ggccagctcc tcaggtggag gcagtagccc aggaccagtt   1140
ccagggagct gcacgggcct ggatggcagg caccctccag ctgggggggg cactgcgtcc   1200
tcgcggcctc tggggcttct atggcttccc tgactgctac aactatgact tctaagccc    1260 caactcacac ggccagtgcc catcaggcat ccgtgcccaa aatgaccagc tagggtggct   1320
gtggggccag agccgtgccc tctatcccag catctacatg cccgcagtgc tggagggcac   1380
agggaagtca cagatgtatg tgcaacaccg tgtggccgag cattccgtg tggctgtggc    1440 tgctggtgac cccaatctgc cggtgctgcc ctatgtccag atcttctatg acacgacaaa   1500
ccactttctg cccctggatg agctggagca cagcctgggg gagagtgcgg cccaggggg    1560 agctggagtg gtgctctggg tgagctggga aaatacaaga accaaggaat catgtcaggc   1620
catcaaggag tatatggaca ctacactggg gcccttcatc ctgaacgtga ccagtggggc   1680
ccttctctgc agtcaagccc tgtgctccgg ccatggccgc tgtgtccgcc gcaccagcca   1740
ccccaaagcc ctcctcctcc ttaacccctgc cagtttctcc atccagctca cgcctggtgg   1800 tggcccctg agcctgcggg gtgccctctc acttgaagat caggcacaga tggctgtgga   1860
gttcaaatgt cgatgctacc ctggctggca ggcaccgtgg tgtgagcgga agagcatgtg   1920
gtgattggcc acacactgag ttgcacatat tgagaaccta atgcactctg ggtctggcca   1980
gggcttcctc aaatacatgc acagtctac aagtcatggt cacagtaaag agtacactca   2040
gccactgtca caggcatatt ccctgcacac acatgcatac ttacagactg gaatagtggc   2100
ataaggagtt agaaccacag cagacaccat tcattcctgc tccatatgca tctacttggc   2160
aaggtcatag acaattcctc cagagacact gagccagtct ttgaactgca gcaatcacaa   2220
aggctgacat tcactgagtg cctactcttt gccaatcccc gtgctaagcg tttatgtgg    2280 acttattcat tcctcacaat gaggctatga ggaaactgag tcactcacat tgagagtaag   2340
cacgttgccc aaggttgcac agcaagaaaa gggagaagtt gagattcaaa cccaggctgt   2400
ctagctccgg gggtacagcc cttgcactcc tactgagttt gtggtaacca gccctgcacg   2460 accccctgaat ctgctgagag gcaccagtcc agcaaataaa gcagtcatga tttactt     2517
```

<210> SEQ ID NO 5
<211> LENGTH: 20
<212> TYPE: DNA
<213> ORGANISM: Homo sapiens

<400> SEQUENCE: 5

-continued

```
caggttgtcc tgcaccagtc                                              20

<210> SEQ ID NO 6
<211> LENGTH: 21
<212> TYPE: DNA
<213> ORGANISM: Homo sapiens

<400> SEQUENCE: 6
atgtgcaact cagtgtgtgg c                                            21

<210> SEQ ID NO 7
<211> LENGTH: 18
<212> TYPE: DNA
<213> ORGANISM: Homo sapiens

<400> SEQUENCE: 7
gtgccatggc aggccacc                                                18

<210> SEQ ID NO 8
<211> LENGTH: 20
<212> TYPE: DNA
<213> ORGANISM: Homo sapiens

<400> SEQUENCE: 8
atcaccacat gctcttccgc                                              20

<210> SEQ ID NO 9
<211> LENGTH: 4
<212> TYPE: PRT
<213> ORGANISM: Artificial Sequence
<220> FEATURE:
<221> NAME/KEY: VARIANT
<222> LOCATION: (1)...(4)
<223> OTHER INFORMATION: Xaa = Any Amino Acid
<220> FEATURE:
<223> OTHER INFORMATION: consensus sequence

<400> SEQUENCE: 9

Cys Ala Ala Xaa
 1

<210> SEQ ID NO 10
<211> LENGTH: 8
<212> TYPE: PRT
<213> ORGANISM: Homo sapiens

<400> SEQUENCE: 10

Phe Arg Gly Pro Leu Leu Val Pro
 1               5

<210> SEQ ID NO 11
<211> LENGTH: 509
<212> TYPE: PRT
<213> ORGANISM: Homo sapiens

<400> SEQUENCE: 11

Met Gly Val Leu Lys Phe Lys His Ile Phe Phe Arg Ser Phe Val Lys
 1               5                  10                  15

Ser Glu Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Ala
            35                  40                  45

Phe Leu Trp Ala Trp Asn Ala Pro Ser Glu Phe Cys Leu Gly Lys Phe
```

```
                    50                  55                  60
Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
                115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
                180                 185                 190

Glu Lys Ala Gly Lys Asp Phe Leu Val Glu Thr Ile Lys Leu Gly Lys
                195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
                275                 280                 285

Ser Lys Ile Pro Asp Ala Lys Ser Pro Leu Pro Val Phe Ala Tyr Thr
                290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
                370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
                450                 455                 460

Ile Asp Ala Phe Leu Lys Pro Pro Met Glu Thr Glu Glu Pro Gln Ile
465                 470                 475                 480
```

```
Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500             505
```

HUMAN PLASMA HYALURONIDASE

CROSS REFERENCE TO RELATED APPLICATIONS

This application is a continuation of U.S. patent application Ser. No. 09/795,914, filed Feb. 27, 2001, now U.S. Pat. No. 7,148,201 which is a continuation of U.S. patent application Ser. No. 08/916,935, filed Aug. 21, 1997, now U.S. Pat. No. 6,193,963, which is a continuation-in-part of U.S. application Ser. No. 08/733,360, filed Oct. 17, 1996, now U.S. Pat. No. 6,103,525, which applications are hereby incorporated by reference.

STATEMENT REGARDING FEDERALLY SPONSORED RESEARCH OR DEVELOPMENT

This invention was made with government support under grant nos. CA44768, CA58207, and GM46765, awarded by the National Institutes of Health. The government may have certain rights in this invention.

FIELD OF THE INVENTION

This invention relates generally to the field of β-1,4-endoglycosidases, particularly hyaluronidases.

BACKGROUND OF THE INVENTION

Hyaluronidases (HAses; E.C. 3.1.25) are a group of neutral- and acid-active enzymes found throughout the animal kingdom in organisms as diverse as microbes (e.g., *Streptococcus pyogenes, Treponema palladium*, and nematodes), bees, wasps, hornet, spiders, scorpions, fish, snakes, lizards, and mammals. Hyaluronidases degrade hyaluronan (HA; also known as hyaluronic acid) and, to a lesser extent, chondroitin sulfates (for a review, see Kreil et al. 1995 *Protein Sci.* 4:1666-9). Vertebrate hyaluronidases are separated into two general classes: 1) the neutral hyaluronidases, such as the predominantly sperm-associated protein PH20 (Liu et al. 1996 *Proc. Natl. Acad. Sci. USA* 93:7832-7; Primakoff et al. 1985 *J. Cell Biol.* 101:2239-44; Lin et al. 1993 *Proc. Natl. Acad. Sci. USA* 90:10071-5); and 2) the acid-active hyaluronidases, which have a distinct pH optimum between pH 3.5 to 4.0 and have been described in extracts of liver (Fiszer-Szafarz et al. 1995 *Acta Biochim Pol.* 42:31-3), kidney (Komender et al. 1973 *Bull. Acad. Pol. Sci. [Biol.]* 21:637-41), lung (Thet et al. 1983 *Biochem. Biophys. Res. Commun.* 117:71-7), brain (Margolis et al. 1972 *J. Neutrochem.* 19:2325-32), skin (Cashman et al. 1969 *Arch. Biochem. Biophys.* 135:387-95), placenta, macrophages, fibroblasts (Lien et al. 1990 *Biochim Biophys. Aca* 1034:318-25; Ruggiero et al. 1987 *J. Dent. Res.* 66:1283-7), urine (Fiszer-Szafarz et al. supra) and human plasma (De Salegui et al. 1967 *Arch. Biochem. Biophys.* 120:60-67). Acid-active hyaturonidase activity has also been described in the sera of mammals, though some species exhibit no detectable activity at all (Fiszer-Szafarz et al. 1990 *Biol. Cell* 68:95-100; De Salegui et al. 1967 supra).

Hyaluronan, the main substrate for hyaluronidase, is a repeating disaccharide of $[GlcNAc\beta1\text{-}4GlcUA\beta1\text{-}3]_n$ that exists in vivo as a high molecular weight linear polysaccharide. Degradation of hyaluronan by hyaluronidase is accomplished by either cleavage at β-N-acetyl-hexosamine-[1→4]-glycosidic bonds or cleavage at β-gluconorate-[1→3]-N-acetylglucosamine bonds.

Hyaluronan is found in mammals predominantly in connective tissues, skin, cartilage, and in synovial fluid. Hyaluronan is also the main constituent of the vitreous of the eye. In connective tissue, the water of hydration associated with hyaluronan creates spaces between tissues, thus creating an environment conducive to cell movement and proliferation. Hyaluronan plays a key role in biological phenomena associated with cell motility including rapid development, regeneration, repair, embryogenesis, embryological development, wound healing, angiogenesis, and tumorigenesis (Toole 1991 *Cell Biol. Extracell. Matrix*, Hay (ed), Plenum Press, New York, 1384-1386; Bertrand et al. 1992 *Int. J. Cancer* 52:1-6; Knudson et al, 1993 *FASEB J.* 7:1233-1241). In addition, hyaluronan levels correlate with tumor aggressiveness (Ozello et al. 1960 *Cancer Res.* 20:600-604; Takeuchi et al. 1976, *Cancer Res.* 36:2133-2139; Kimata et al. 1983 *Cancer Res.* 43:1347-1354).

Hyaluronidase is useful as a therapeutic in the treatment of diseases associated with excess hyaluronan and to enhance circulation of physiological fluids and/or therapeutic agents at the site of administration. For example, hyaluronidase has been used to reduce intraocular pressure in the eyes of glaucoma patients through degradation of hyaluronan within the vitreous humor (U.S. Pat. No. 4,820,516, issued Apr. 11, 1989). Hyaluronidase has also been used in cancer therapy as a "spreading agent" to enhance the activity of chemotherapeutics and/or the accessibility of tumors to chemotherapeutics (Schüller et al., 1991, *Proc. Amer. Assoc. Cancer Res.* 32:173, abstract no. 1034; Czejka et al., 1990, *Pharmazie* 45:H.9) and has been used in combination with other chemotherapeutic agents in the treatment of a variety of cancers including urinary bladder cancer (Horn et al., 1985, *J. Surg. Oncol.,* 28:304-307), squamous cell carcinoma (Kohno et al., 94, *J. Cancer Res. Oncol.,* 120:293-297), breast cancer (Beckenlehner et al., 1992, *J. Cancer Res. Oncol.* 118:591-596), and gastrointestinal cancer (Scheithauer et al., 1988, *Anticancer Res.* 8:391-396). Administration of hyaluronidase also induces responsiveness of previously chemotherapy-resistant tumors of the pancreas, stomach, colon, ovaries, and breast (Baumgartner et al., 1988, *Reg. Cancer Treat.* 1:55-58; Zänker et al., 1986, *Proc. Amer. Assoc. Cancer Res.* 27:390). Serum hyaluronidase prevents growth of tumors transplanted into mice (De Maeyer et al., 1992, *Int. J. Cancer* 51:657-660), while injection of hyaluronidase inhibits tumor formation caused by exposure to carcinogens (Pawlowski et al., 1979, *Int. J. Cancer* 23:105-109; Haberman et al., 1981, *Proceedings of the 17the Annual Meeting of the American Society of Clinical Oncology*, Washington, D.C., 22:105, abstract no. 415). Intravenous or intramuscular injection of hyaluronidase is effective in the treatment of brain cancer (gliomas) (PCT published application no. WO88/02261, published Apr. 7, 1988).

Hyaluronidase expression, and levels of hyaluron, have been associated with tumor development and progression. Levels of a secreted neutral hyaluronidase activity in carcinomas derived from ovary (Miura et al. 1995 *Anal. Biochem.* 225:333-40), prostate (Lokeshwar et al. 1996 *Cancer Res* 56:651-7), brain, melanocyte, and colon (Liu et al. 1996 *Proc. Natl. Acad. Sci. USA* 22:7832-7837) are higher than in normal tissue. This secreted neutral hyaluronidase activity appears similar or identical to the neutral hyaluronidase activity of the sperm hyaluronidase PH20. In contrast to neutral activity, the acid active serum hyaluronidase activity is significantly decreased in metastatic carcinomas of the lung, breast, and colon (Northrup et al. 1973 *Clin. Biochem.* 6:220-8; Kolarova et al. 1970 *Neoplasma* 17:641-8). Further, mice having an allele of the hyal-1 locus that is associated with lower levels of serum hyaluronidase activity exhibit faster rates of growth of transplanted tumors than mice having an hyal-1 allele that is associated with 3-fold higher hyaluronidase activity levels (Fiszer-Szafarz et al. 1989 *Somat. Cell. Mol. Genet.* 15:79-83; De Maeyer et al. supra).

At present, the only hyaluronidase activity available for clinical use is a hyaluronidase isolated from a testicular extract from cattle (WYDASE®, Wyeth-Ayerst). The bovine extract is not optimum not only because of its non-human source, but also because the extract contains multiple types of hyaluronidases and other as yet undefined components. While the human serum acid-active hyaluronidase activity would be preferred for administration, this hyaluronidase has not been previously isolated or purified. Although previous studies were able to determine that the serum acid-active hyaluronidase activity is not a component of platelets since hyaturonidase activity levels in plasma are comparable to those found in serum (De Salegui et al. 1967 supra), attempts to isolate this acid active hyaluronidase activity from human serum have met with limited success due in part to the stability of the purified activity and the inability to obtain an adequately high specific activity. Immunopurification attempts have been hindered by the inability to identify and isolate antibodies that specifically bind the activity in its native form in plasma. Monoclonal antibodies identified by conventional ELISA techniques bind denatured human plasma hyaluronidase in the ELISA screening assay do not bind the native, folded protein (Harrison et al. 1988 *J Reprod Fertil* 82:777-85).

Conventional methods for hyaluronidase activity include ELISA-like assays (Delpech et al. 1987 *J. Immunol. Methods* 104:223-9; Stern et al. 1992 *Matrix* 12:397-403; Afify et al. 1993 *Arch. Biochem. Biophys.* 104:434-41; Reissig et al., 1955, *J. Biol. Chem.* 21:956-966) in which a sample containing hyaluronidase is applied to the well of a microtiter dish having hyaluronan or hyaluroneetin non-covalently bound to its surface. HAse present in the sample degrades the HA substrate. The plates are then washed, and HAse activity is detected by examining the plates for remaining HA substrate.

Hyaluronidase activity can also be detected by substrate gel zymography (Guentenhoner et al., 1992, *Matrix* 12:388-396). In this assay a sample is applied to a SDS-PAGE gel containing hyaluronan and the proteins in the sample separated by electrophoresis. The gel is then incubated in an enzyme assay buffer and subsequently stained to detect the hyaluronan in the gel. Hyaluronidase activity is visualized as a cleared zone in the substrate gel.

These conventional methods for detecting hyaluronidase activity are hampered by both the difficulties in producing a detectably-labeled hyaluronic acid substrate and the technical difficulties in achieving rapid, sensitive, and reproducible detection of hyaluronidase activity. For example, biotin labeling of hyaluronic acid for use in ELISA-like assays has proved reticent to biotinylation since HA contains no free amine groups, the moiety with which activated biotin covalently binds. Prior attempts to solve this problem have focused on use of a biotinylated-HA binding aggrecan peptide from bovine nasal cartilage (Levvy et al. 1966 *Method Enzymol.* 8:571-584), which requires tedious, time-consuming steps.

Furthermore, conventional hyaluronidase assays use assay plates having HA substrate non-covalently bound to the plate surface, which can lead to both false positive and false negative results. Because the HA substrate is non-covalently bound to the plate surface, the washing step following exposure of the plates to the HAse-containing sample often results in non-specific removal of non-degraded HA substrate on the plate. Thus, the sensitivity of the conventional HAse assay is compromised. HAse activities using gel zymography avoid the problem associated with ELISA-like assays, but are time-consuming (e.g., the test sample and the HA-containing gel are normally incubated for about 18 hr to 24 hr) and can result in artifacts if the gel is improperly loaded with excess protein sample. Moreover, analyses of crude preparations is impossible by gel zymography.

Thus, despite the presence of a desirable acid active plasma hyaluronidase activity, and human blood product companies' economic motivation to obtain any and all useful components from a resource as precious and scarce as human blood, the human plasma fractions containing this acid active hyaluronidase activity are discarded for want of an acceptable method for its isolation and purification.

Given the value of hyaluronidases in chemotherapy, there is a need in the field for a method of identifying and isolating the polypeptide associated with the acid active hyaluronidase activity in human serum.

SUMMARY OF THE INVENTION

The invention is based on the discovery of methods for purification of an acid active hyaluronidase found in human plasma (hpHAse), which include both biochemical and immunoaffinity purification methods. The method of immunoaffinity purification of the invention is based on the discovery of a method for identifying antibodies that specifically bind native hpHAse (anti-native hpHAse antibodies), and anti-native hpHAse antibodies identified by this screening method. The invention also features an assay for sensitive detection of HAse activity using biotinylated hyaluronic acid (bHA). Purification and characterization of hpHAse lead to the inventors' additional discovery that hpHAse is encoded by the LuCa-1 gene, which is located in the human chromosome at 3p21.3, a region associated with tumor suppression.

Thus, in one aspect the invention features an assay device for detection of hyaluronidase activity comprising an insoluble support and biotinylated hyaluronic acid (bHA) covalently bound to the support. Preferably, the bHA is prepared in a one-step reaction of hyaluronic acid, 1-ethyl-dimethylaminopropyl carbodiamide (EDC), and biotin hydrazide. In preferred embodiments, the bHA comprises at least one biotin moiety per every 100 disaccharide units in the hyaluronic acid moiety, and the bHA is covalently bound to the support by at least one covalent bond per every 50 disaccharide units in the hyaluronic acid moiety.

In another aspect the invention features a method of purifying a native acid active hyaluronidase (aaHAse) from a sample, the method comprising the steps of: (a) dissolving a sample suspected of containing aaHAse in a solution at a temperature substantially less than room temperature, the solution comprising a non-ionic detergent; (b) raising the temperature of the solution to a temperature substantially greater than room temperature, said raising resulting in the formation of a detergent-rich phase comprising aaHAse and a detergent-poor phase; and (c) isolating aaHAse from the detergent-rich phase. Preferably the aaHAse is hpHAse and steps (a)-(c) are repeated twice.

In yet another aspect of the invention, the invention features a method for screening candidate antibodies for binding to a native aaHAse comprising the steps of: (a) incubating a candidate antibody with a sample comprising native aaHAse, said incubating being for a time sufficient for formation of antibody-aaHAse complexes; (b) contacting the sample with an insoluble support having anti-antibody and detectably-labeled hyaluronic acid bound thereto for a time sufficient for formation of anti-antibody-candidate antibody-hpHAse complexes; and (c) exposing the sample in contact with the support to an acidic pH of about 3.4 to 3.7, thereby allowing hpHAse in the antibody-aaHAse complex to degrade the detectably labeled hyaluronic acid, wherein samples associated with hyaluronic acid degradation comprise an anti-aa-HAse antibody. In related aspects, the invention features anti-native hpHAse antibodies, hybridoma cell lines secreting such antibodies, and assay devices for immunopurification and/or detection of hpHAse comprising anti-hpHAse antibodies bound thereto.

In still another aspect, the invention features a method of purifying hpHAse from a sample, the method comprising contacting a sample comprising hpHAse with an anti-hpHAse antibody. In preferred embodiments, the sample is human blood, serum, plasma, or urine or the hpHAse is a recombinant hpHAse.

In another aspect, the invention features substantially purified native hpHAse characterized by a fatty acid moiety that is resistant to cleavage by phospholipase C, phospholipase D, and N-glycosidase-F. In related aspects the invention features formulations comprising native hpHAse, particularly liposome formulations.

In yet another aspect the invention features methods for recombinantly expressing hpHAse. The recombinant expression system of the invention provides high levels of secreted hpHAse suitable for commercial production of hpHAse and for production of hpHAse for use in therapeutic applications. In related aspects the invention features recombinant hpHAse and methods of making recombinant hpHAse.

In additional related aspects, the invention features methods of treating patients having or susceptible to a condition for which administration of hyaluronidase is desirable. In specific embodiments, the invention features administration of human plasma hyaluronidase to a patient having or susceptible to cancer associated with defective hpHAse expression comprising administering hpHAse polypeptide to the patient in an amount effective to suppress tumor growth. In further embodiments, the invention features methods of treating a patient after suffering a myocardial infarction or a patient suffering from a lysosomal storage disease.

Another aspect of the invention features a method of treating a patient having or susceptible to cancer associated with a defective LuCa-1 gene, the method comprising introducing into a cell of the patient a construct comprising a nucleotide sequence encoding a human plasma hyaluronidase polypeptide and a eukaryotic promoting sequence operably linked thereto, resulting in the genetic transformation of the cell so that the nucleotide sequence expresses hpHAase.

The invention also features a method for identifying a patient having or susceptible to a condition associated with defective human plasma hyaluronidase activity comprising the steps of contacting a plasma sample from the patient with an anti-native human plasma hyaluronidase antibody and detecting complexes of the enzyme and the antibody.

A primary object of the invention is to provide a purified hyaluronidase, hpHAse, which can be used in a variety of clinical therapies including cancer therapy, particularly cancers associated with a defect in the tumor suppressor gene LuCa-1.

An advantage of the present invention is that purified hpHAse is more appropriate for therapeutic uses than the presently available commercial formulations of hyaluronidase which are from a non-human source, which contain two hyaluronidases (rather than one), and which, as determined by SDS-PAGE analysis, is a very crude mixture that contains various proteins, including several unidentified proteins and proteins having various biological activities including anticoagulant activities (Doctor et al., Thrombosis Res.

30:565-571). Purified hpHAse provides a "clean" source of hyaluronidase, is less likely to induce some of the side effects associated with the presently available commercial formulation, and allows better control of the level of activity associated with specific dosages.

Another advantage of the invention is that hpHAse can be purified from a lipid fraction of plasma that, according to present commercial practices, is otherwise discarded.

An advantage of the HAse assay of the invention is that it provides for an assay for HAse activity that is at least 1,000-fold more sensitive than conventional ELISA-like assays. In addition, the invention provides a biotinylated hyaluronic acid substrate that can be easily and efficiently prepared.

An advantage of the anti-native aaHAse assay of the invention is that the assay provides a rapid screen for antibodies that bind native aaHAse.

Another advantage of the invention is that specific detection of hpHAse allows a specific means of measuring LuCa-1 expression and correlation of levels of hpHAse in serum or urine of a patient with susceptibility to or presence of a disease associated with a LuCa-1 defect (e.g., cancer, e.g., small cell lung cell carcinoma).

These and other objects, advantages and features of the present invention will become apparent to those persons skilled in the art upon reading the details of the invention as more fully set forth below.

BRIEF DESCRIPTION OF THE DRAWINGS

FIG. 5 is a schematic showing the alignment of the predicted amino acid sequence of LuCa-1 with the amino acid sequence of the neutral HAse PH20. Identical amino acid residues are shaded.

DETAILED DESCRIPTION OF THE PREFERRED EMBODIMENTS

Figure 1:
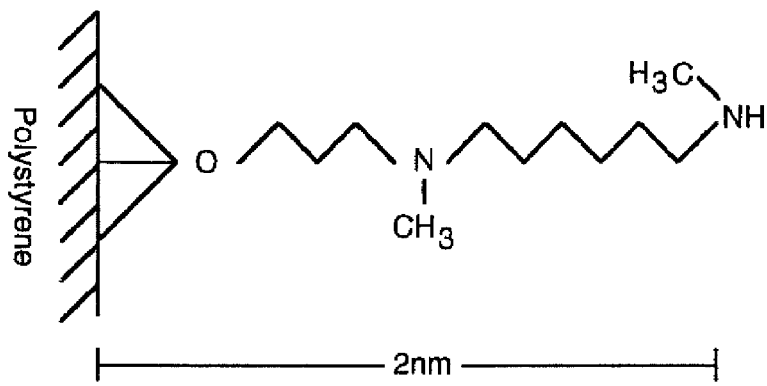
FIG. 1 is a schematic showing the chemical and physical configuration of a surface for covalent attachment of biotinylated HA.

Before the present purified hyaluronidase and DNA encoding same are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a transformed cell containing DNA encoding a hyaluronidase" includes a plurality of such cells and reference to "the transformation vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

DEFINITIONS

By "acid active hyaluronidase" or "aaHAse" is meant a hyaluronidase having β-1,4-endoglycosidase activity in the cleavage of hyaluronan and a pH optimum of HAse activity at about pH 3.7. aaHAse as used herein encompasses human plasma hyaluronidase.

By "human plasma hyaluronidase," "human plasma acid active hyaluronidase," and "hpHAse" is meant a hyaluronidase naturally found in human plasma and having the following characteristics: 1) β-1,4-endoglycosidase activity in the cleavage of hyaluron; 2) a pH optimum of HAse activity at about pH 3.7; 3) a molecular weight of about 57 kDa as determined by 12.5% SDS-PAGE non-reducing gel electrophoresis; 4) a specific enzymatic activity of about $2\times10^5$ to $8\times10^5$ turbidity reducing units (TRU)/mg protein following purification; 5) an isoelectric point, as determined by elution in chromatofocusing on Mono-P f.p.l.c., of pH 6.5; 6) partitioning into the Triton X-114 detergent-rich phase upon temperature-induced detergent phase extraction; 7) a fatty acid post-translational modification (e.g., a lipid anchor) that is resistant to cleavage by phospholipase C, phospholipase D, and N-glycosidase-F; 8) at least two N-linked glycosylation sites; and 9) has the amino acid sequence:

```
                                          (SEQ ID NO: 1)
MAGHLLPICALFLTLLDMAQGFRGPLLPNRPFTTVWNANTQWCLERHGVD
VDVSVFDVVANPGQTFRGPDMTIFYSSQLGTYPYYTPTGEPVFGGLPQNA
SLIAHLARTFQDILAAIPAPDFSGLAVIDWEAWRPRWAFNWDTKDIYRQR
SRALVQAQHPDWPAPQVEAVAQDQFQGAARAWMAGTLQLGGALRPRGLWG
FYGFPDCYNYDFLSPNTYGQCPSGIRAQNDQLGWLWGQSRALYPSIYMPA
VLEGTGKSQMYVQHRVAEAFRVAVAAGDPNLPVLPYVQIFYDTTNHFLPL
DELEHSLGESAAQGAAGVVLWVSWENTRTKESCQAIKEYMDTTLGPFILN
VTSGALLCSQALCSGHGRCVRRTSHPKALLLLNPASFSIQLTPGGGPLSL
RGALSLEDQAQMAVEFKCRCYPGWQAPWCERKSMW
``` where MAGHLLPICALFLTLLDMAQG (SEQ ID NO:2) is a signal sequence cleaved during post-translational modification. "hpHAse" as used herein is meant to encompass hpHAse polypeptides having the amino acid sequence of naturally-occurring hpHAse, as well as hpHAse polypeptides that are modified relative to the naturally-occurring amino acid sequence due to amino acid substitution, deletion, and/or addition (e.g., fusion proteins) and the like. Preferably, "hpHAse" encompasses hpHAse polypeptides that are biologically active (e.g., can bind anti-hpHAse antibodies and/or exhibit hyaluronidase activity).

By "urine form of hpHAse" or "urine hpHAse" is meant a form of hpHAse is found in human urine and characterized by: 1) β-1,4-endoglycosidase activity in the cleavage of hyaluron; 2) a pH optimum of HAse activity at about pH 3.7; 3) a molecular weight of about 57 kDa as determined by gel zymography using 12.5% SDS-PAGE non-reducing gel electrophoresis; 4) immunoprecipitation with anti-native hpHAse monoclonal antibodies specific to LuCa-1; 5) an isoelectric point, as determined by elution in chromatofocusing on Mono-P f.p.l.c., or pH 6.5; and 6) partitioning into the Triton X-114 detergent-rich phase upon temperature-induced detergent phase extraction.

By "native hpHAse" is meant hpHAse that is folded in its naturally-occurring configuration (i.e., hpHAse is not denatured). Where the native hpHAse does not comprise the entire amino acid sequence of naturally-occurring hpHAse, native hpHAse polypeptides are those potypeptides that, when folded, mimic a three-dimensional epitope of native, full-length hpHAse such that antibodies that bind native hpHAse bind to the hpHAse polypeptide. "Native hpHAse" encompasses both hpHAse that is naturally found in human plasma, blood, serum, and urine, as well as hpHAse that is recombinantly produced (e.g., by expression in a mammalian cell).

By "polypeptide" is meant any chain of amino acids, regardless of length or post-translational modification (e.g., glycosylation, phosphorylation, or fatty acid chain modification).

By a "substantially pure polypeptide" a polypeptide that has been separated from components which naturally accompany it (e.g., a substantially pure hpHAse polypeptide purified from human plasma is substantially free of components normally associated with human plasma). Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, hpHAse polypeptide. A substantially pure hpHAse polypeptide can be obtained, for example, by extraction from a natural source (e.g., mammalian plasma, preferably human plasma); by expression of a recombinant nucleic acid encoding hpHAse polypeptide; or by chemically synthesizing the protein, Purity can be measured by any appropriate method, e.g., chromatography, polyaprylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By "antibody" is meant an immunoglobulin polypeptide that is capable of binding an antigen. Antibody as used herein is meant to include the entire antibody as well as any antibody fragments (e.g. F(ab')$_2$, Fab', Fab, Fv) capable of binding the epitope, antigen or antigenic fragment of interest. Antibodies of the invention are immunoreactive or immunospecific for and therefore specifically and selectively bind to native hpHAse polypeptide. Anti-hpHAse antibodies are preferably immunospecific (i.e., not substantially cross-reactive with related materials). Antibodies may be polyclonal or monoclonal, preferably monoclonal.

By "binds specifically" is meant high avidity and/or high affinity binding of an antibody to a specific polypeptide i.e., epitope of hpHAse. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to hpHAse than to other components in human plasma. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound or polypeptide of interest, e.g. by use of appropriate controls. In general, antibodies of the invention which bind to native hpHAse with a binding affinity of $10^7$ liters/mole or more, preferably $10^8$ l/mole or more, even more preferably $10^9$ l/mole or more, are said to bind specifically to hpHAse. In general, an antibody with a binding affinity of $10^4$ l/mole or less is not useful in that it will not bind an antigen at a detectable level using conventional methodology currently used.

By "anti-native hpHAse antibody" or "anti-hpHAse antibody" is meant an antibody that specifically binds native (i.e., non-denatured) hpHAse. Preferably, such antibodies can be used to immunopurify (e.g., by immunoprecipitation or immunoaffinity column chromatography) naturally-occurring hpHAse from human plasma and/or recombinant hpHAse expressed by, for example, mammalian cells.

By "operably linked" is meant that a DNA of interest (e.g., DNA encoding an hpHAse polypeptide) and a regulatory sequence(s) are connected in such a way as to permit gene expression of the DNA of interest when the appropriate molecules (e.g., transcriptional activator proteins) are bound to the regulatory sequence(s), thus facilitating production of, e.g., an hpHAse polypeptide, a recombinant protein, or an RNA molecule.

By "transformation" is meant a permanent genetic change induced in a cell following incorporation of new DNA (i.e., DNA exogenous to the cell). Where the cell is a mammalian cell, the permanent genetic change is generally achieved by introduction of the DNA into the genome of the cell.

By "vector" is meant any compound, biological or chemical, which facilitates transformation of a host cell with DNA encoding an hpHAse polypeptide of the invention.

By "substantially identical" is meant a polypeptide or nucleic acid exhibiting at last 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease (e.g., cancer) from occurring in a subject who may be predisposed to the disease but has not yet been diagnosed as having it; (b) inhibiting the disease, i.e., arresting its development; or (e) relieving the disease, i.e., causing regression of the disease (e.g, reduction in tumor volume, slowing of cachexia). The invention is directed toward treatment of patients having or susceptible to cancer associated with a defect in the LuCa-1 gene, the gene that encodes hpHAse.

By "therapeutically effective amount of a substantially pure hpHAse polypeptide" is meant an amount of a substantially pure hpHAse polypeptide effective to facilitate a desired therapeutic effect. The precise desired therapeutic effect will vary according to the condition to be treated. For example, the desired degradation of hyaluronan is the desired therapeutic effect where hpHAse is administered to the subject in the treatment of a condition associated with excess hyaluron, undesirable cell motility (e.g., tumor cell metastasis), and/or to enhance circulation of physiological fluids at the site of administration and/or inhibit tumor growth or progression. Where hpHAse is administered to treat a patient having or susceptible to cancer associated with a LuCa-1 defect, one desired therapeutic effects include, but are not necessarily limited to, an inhibition of tumor cell growth and a decrease in the tumor cell's threshold to apoptosis (i.e., increase the cell's sensitivity to triggers to programmed cell death). Therapeutic effects of hpHAse may be associated with hpHAse's hyaluronidase activity, chondroitanase activity, or both.

By "LuCa-1 defect" or "hpHAse defect" is meant a genetic defect in a cell at chromosome position 3p.21.3 associated with a decreased level of hpHAse activity relative to hpHAse activity levels in normal cells and/or a decreased level of hpHAse activity in the serum or plasma of the affected patient (e.g., due to decreased expression of hpHAse or expression of a defective hpHAse). "LuCa-1 defect" or "hpHAse defect" are also meant to encompass cellular defects associated with a decreased level of hpHAse activity in the serum or plasma of the affected patient (e.g., a defect in transport of hpHAse into the bloodstream). For example, plasma from patients have a LuCa-1 defect-associated lung cancer exhibits about 50% less hpHAse activity than plasma from normal patients (i.e., patients who do not have a LuCa-1 defect-associated cancer). Normal human plasma exhibits about 15 rTRU/mg hpHAse activity as determined using the HAse assay of the invention. The hpHAse activity of plasma from LuCa-1 defect-associated lung cancer patients is about 7.5 rTRU/mg.

By "having or susceptible to a condition associated with a LuCa-1 defect" is meant to describe a patient having a heterozygous, homozygous, or epigenetic defect at the LuCa-1 locus and/or some other genetic defect outside the LuCa-1 locus associated with decreased levels of hpHAse (e.g., serum hpHAse or urine hpHAse, preferably serum hpHAse) relative to hpHAse levels associated with normal patients (i.e., patients having no LuCa-1 defect that results in altered hpHAse levels). Exemplary patients having or susceptible to a condition associated with a LuCa-1 defect are patients bearing tumor or pre-tumor cells that do no express normal levels of hpHAse (e.g., a metatstatic carcinoma).

The invention will now be described in further detail.

Hyaluronidase Activity Assay

The HAse assay of the invention involves labeling of HA by biotinylation of free carboxyl groups through a simple, one step reaction with 1-ethyl-dimethylaminopropyl carbodiamide (EDC, $ClCH_2CH_2Cl$, Sigma) and biotin hydrazide (Pierce). Briefly, a solution composed of dissolved HA and dissolved biotin hydrazide is combined with EDC. Preferably, biotin is present in excess relative to EDC and HA. The molar amount of EDC present is varied according to the desired number of covalent bonds to be found between the carboxyl groups of the disaccharide units of HA and the NH groups of the biotin moieties (i.e, the desired number of biotin moieties relative to the number of HA disaccharide units). Preferably, the molar ratio of HA disaccharide units to EDC is 85:1, while the molar ratio of biotin hydrazide to EDC is 38:1. An exemplary chemical structure of the resulting HA-bHA compound is shown in FIG. 1.

After the HA-EDC-biotin hydrazide reaction is complete, uncoupled biotin can be removed through dialysis, preferably dialysis against distilled water. The biotinylated HA substrate (bHA) that results comprises an EDC-biotin moiety covalently bound to the HA molecule at a ratio of 1 EDC-biotin moiety for every 200 disaccharide moieties, preferably every 150 disaccharide moieties, more preferably every 85 to 100 disaccharide units in the HA molecule. The ratio of EDC-biotin to HA molecule can range from as high as 1:1 (e.g., one EDC-biotin moiety bound to a disaccharide unit) to 5:1 (e.g., one EDC-biotin moiety bound to an HA molecule containing 100 disaccharide units). The bHA reagent can be stored, preferably at −20° C., until use.

Figure 2:
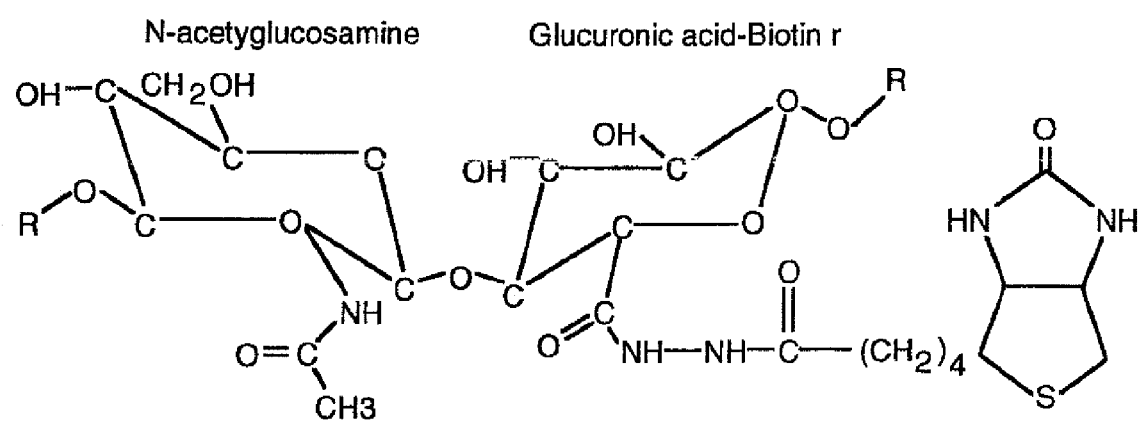
FIG. 2 is a schematic showing the chemical structure of biotinylated HA.

Assay devices for detection of HAse activity are prepared by coupling bHA to, for example, the surface of a microtiter well having a covalently attached moiety $NH-CH_3$ (e.g., Covalink-NH microtiter plates, NUNC, Placerville, N.J.). An exemplary chemical and physical configuration of surface for covalent attachment is shown in FIG. 2. Methods for preparation of such substrates and the use of such substrates to covalently immobilize compounds are well known in the art (see, e.g., U.S. Pat. No. 5,427,779, issued Jun. 27, 1996, and PCT published application number WO 8905329, published Jun. 15, 1989). Coupling of bHA to the assay device is accomplished by, for example, incubation of bHA in the Covalink-NH well with EDC according to the manufacturer's specifications. Unbound bHA is removed by washing the wells with buffer. bHA that remains in the well of the plate is covalently bound to the surface of the well. The resulting assay device comprises bHA covalently bound to the surface to be exposed to the test sample such that the bHA is bound to the surface by at least one covalent bond, preferably at least one covalent bond per every 200 disaccharide units in the bHA molecule, more preferably at least one covalent bond per 100 disaccharide units, most preferably at least one covalent bond per 50 disaccharide units in the bHA molecule. The plates are preferably used within about 1 week to 10 days after preparation.

The HAse activity assay is performed by placing a test sample in the well of the assay device having covalently-bound bHA, and incubating the sample for a period sufficient to allow for hpHAse in the test sample to degrade bHA in the well. The test sample can be any sample suspected of having HAse activity (e.g., a biological sample (e.g., blood, serum, plasma, urine, or a sample derived from a recombinant source) or a sample from a step during biochemical purification). Preferably, a sample having a known amount of hpHAse activity is subjected to the assay as a control.

The pH of the incubation buffer can be adjusted according to the desired ph optima of the HAse activity in the sample (e.g., neutral HAse activity (pH of about 7.0 to 7.5) or acid active HAse activity (pH below about 4.5, preferably at about pH 3.0 to 3.7)). Following incubation, the wells are washed to remove degraded bHA and remaining, undegraded bHA is detected, e.g., by reaction the remaining bHA with avidin peroxidase and detection with a microplate reader. Covalent binding of bHA to the assay device prevents the undegraded bHA from being washed off the plate, thus increasing the sensitivity and accuracy of the assay. Moreover, the assay requires only 60 minutes or less to complete and is 1,000 times more sensitive than conventional colorimetric assays (Afify et al. supra) and about 1,000 to 5,000 times more sensitive than SDS-based gel zymography. The HAse assay of the invention can be used in a variety of applications where one desires to determine (qualitatively or quantitatively) the presence of acid active or neutral HAse activity in a sample. In one embodiment, the HAse activity assay of the invention is useful in the identification of patients having a defect in HAse activity (e.g., a LuCa-1/hpHAse defect associated with reduced hpHAse plasma activity), determine, and/or.

Specific activity of hyaluronidase is expressed in turbidity reducing units (TRU). One TRU is defined as the amount of hyaluronidase activity required to reduce the turbidity of an acidified solution of hyaluronan and is equivalent to the U.S.P./National Formulary (NF XIII) units (NFU). The results using the assays described above are related to the TRU, the NFU, and U.S.P. units through a standard curve of a sample of hyaluronidase (e.g., WYDASE®, Wyeth-Ayerst) standardized through the U.S.P. For example, a standard curve can be generated through co-incubation of serial dilutions of bovine testicular hyaluronidase (WYDASE®) and activity of unknown samples interpolated through a four parameter curve fit to yield values in relative TRU (rTRU)/ml (Dorfman et al., 1948, *J. Biol. Chem.* 172:367).

Biochemical hpHAse Purification Method

Acid active hyaluronidase activity can be significantly enriched and/or purified using temperature-induced detergent phase extraction with a non-ionic detergent (e.g., Triton X-114). In general, a sample comprising or suspected of comprising an acid active HAse (aaHAse) such as hpHAse is dissolved in a solution comprising a non-ionic detergent at low temperature (e.g., substantially below room temperature, preferably less than about 15° C., more preferably about 4° C.). The sample can be, for example, raw human plasma, outdated human plasma without platelet degranulation (e.g., through addition of citrate), a lipid fraction of human plasma, human blood, human serum, human urine, or conditioned medium or lysates from cells expressing recombinant aaHAse (e.g., mammalian, insect, bacterial, or yeast cells, preferably mammalian cells). Preferably, the sample is human plasma or human urine, which is a particularly rich source of hpHAse. Purification from plasma is advantageous over purification from whole blood or serum since the plasma fraction contains less total protein than either serum or whole blood.

After the sample is dissolved, the temperature of the solution is raised to at least room temperature or above (preferably above about 25° C., more preferably about 37° C.), thereby resulting in formation of detergent-rich and detergent-poor phases. The aaHAse partitions into the detergent-rich phase. The detergent-rich phase can be further enriched for aaHAse by removal of the detergent-rich phase and repetition of temperature-induced detergent phase extraction. Repeating this temperature-induced detergent phase extraction three times results in at least about 10-fold, preferably at least about 20-fold, more preferably at least about 60-fold enrichment of aaHAse activity relative to aaHAse activity in the starting material. The aaHAse activity of the detergent-rich phase can be further enriched and purified by, for example, cation exchange chromatography and/or hydroxylapatite resin.

Generation and Identification of Anti-Native aaHAse Antibodies

Although there are known procedures for producing antibodies from any given antigen, previous attempts to produce anti-native aaHAse antibodies (e.g., anti-native hpHAse antibodies) have failed. Although antibodies that bind denatured anti-aaHAse have been generated, these antibodies, generated using conventional methods and a conventional ELISA assay, did not bind native (i.e., non-denatured) aaHAse (Harrison et al. 1988 *J Reprod Fertil* 82:777-85). By following the procedures described herein, antibodies that bind native aaHAse enzymes (e.g., native hpHAse) have been obtained. Likewise, the ordinarily skilled artisan can follow the procedures outlined herein to generate other anti-native aaHAse antibodies, including other anti-native hpHAse antibodies. In general, the invention overcomes the problems associated with production of aaHAse antibodies by providing a screening assay that detects antibodies that bind native aaHAse.

Generation of Anti-hpHAse Antibodies aaHAse can be used as an antigen in the immunization of a mammal (e.g., mouse, rat, rabbit, goat) and production of hybridoma cell lines according to methods well known and routine in the art (see, for example, Harlow and Lane, 1988, *Antibodies: A Laboratory Manual*, Cold Spring Harbor Laboratory Press, Cold Spring Harbor, N.Y.; Schrier et al., 1980, *Hybridoma Techniques*, Cold Spring Harbor Laboratory Press, Cold Spring Harbor, N.Y.). The aaHAse used in the antigenic preparation can be purified from the source in which it naturally occurs (e.g., hpHAse purified from human plasma), recombinant aaHAse, biologically active (e.g., antigenic and/or enzymatically active) aaHAse polypeptides, native aaHAse, and/or denatured aaHAse polypeptides. Where the aaHAse is a recombinant aaHAse, the recombinant aaHAse can comprise the amino acid sequence of a naturally-occurring aaHAse, or can be modified relative to native aaHAse (e.g., by amino acid substitution, deletion, or addition (e.g., fusion protein)). Preferably, the antigenic preparation is native aaHAse (e.g., aaHAse purified from the source in which it naturally occurs or recombinant, full-length aaHAse). aaHAse can be any acid active hyaluronidase; preferably the aaHAse is hpHAse.

Assay for Anti-aaHAse Antibodies

The antibodies secreted by the hybridoma cell lines are screened in the anti-native aaHAse antibody assay of the invention, In general, the assay involves an insoluble support (e.g., the surface of a well of a microtiter plate) to which is bound: 1) an anti-antibody; and 2) detectably labeled hyaluronic acid (HA). The anti-antibody is capable of binding antibodies produced by the aaHAse-immunized mammalian host regardless of antigen specificity. For example, where the immunized host is a mouse, the anti-antibody is a goat anti-mouse antibody (i.e., an antibody from a goat immunized with mouse antibodies). Preferably, the anti-antibody binds an Fc portion of antibodies produced by the aaHAse-immunized mammalian host, and may specifically bind immunoglobulin classes or subclasses (e.g., specifically bind IgG or an IgG subclass such as $IgG_1$ or $IgG_2$). Preferably, the anti-antibody is covalently bound to the surface of the insoluble support. The detectably labeled HA is preferably biotinylated HA (bHA) in the above-described HAse assay, and is preferably covalently bound to the surface of the insoluble plate as described above.

Figure 3:
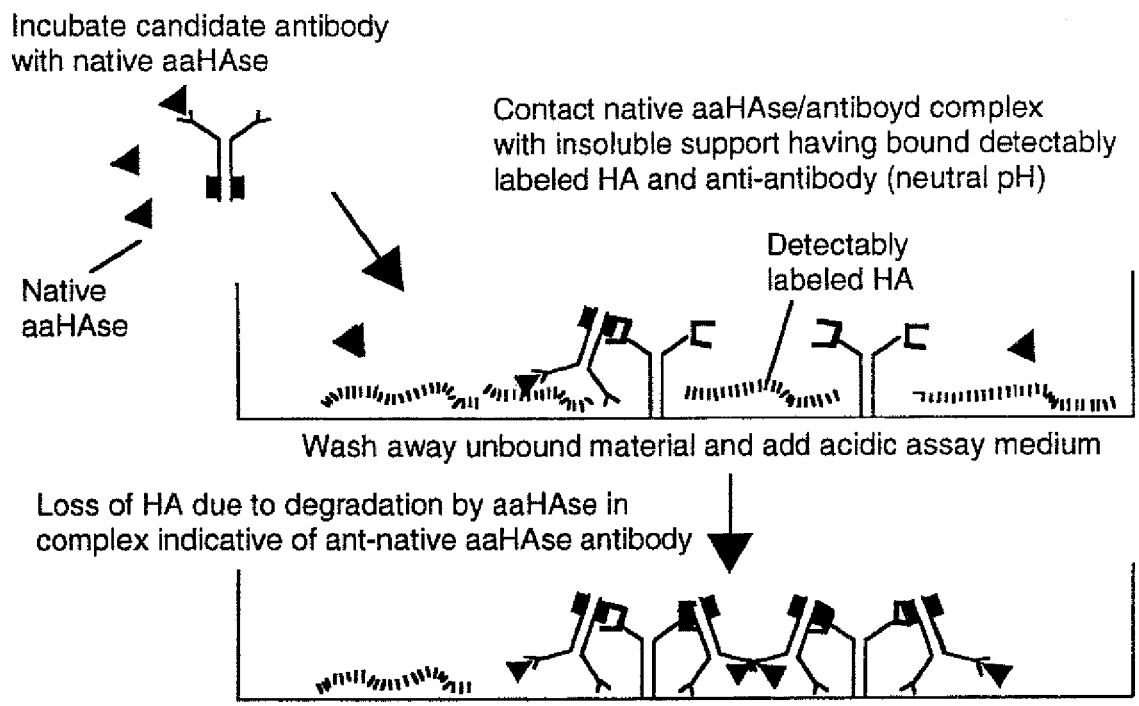
FIG. 3 is a schematic showing the steps in the anti-native acid active HAse antibody assay of the invention.

A schematic of the anti-aaHAse assay of the invention is shown in FIG. 3. The anti-aaHAse antibody assay of the invention takes advantage of the inventors' observation that aaHAses do not bind their HA substrates under non-acidic conditions (i.e., under conditions in which the aaHAse is not enzymaticaly active). In general, the assay is performed by contacting the candidate antibody with a sample comprising native aaHAse (e.g., native hpHAse) to allow for formation of native aaHAse/antibody complexes. Preferably, this contacting step is performed at a non-acidic, preferably neutral, pH. The sample is then contacted under non-acidic (preferably neutral) conditions with the insoluble support having bound anti-antibody and detectably labeled HA to allow for formation of native aaHAse/antibody/anti-antibody complexes by binding of the anti-antibody to the candidate antibody. Preferably, excess or unbound material is washed away with a non-acidic (preferably neutral) solution.

The wash buffer is replaced with an acidic solution having a pH that allows for enzymatic activity of the aaHAse. Preferably the acidic solution has a pH that approximates the optimum pH for HAse activity of the aaHAse. For example, where the aaHAse is hpHAse, the acidic solution preferably has a pH of 3.7. The sample is incubated with the insoluble support for a time sufficient for degradation of the detectably labeled HA by the immunoprecipitated aaHAse bound in the native aaHAse/antibody/anti-antibody complex, preferably about 60 min. The samples are then washed to remove degraded HA and undegraded HA is detected by virtue of its label. For example, where the detectable label is biotin, undegraded bHA is detected as described in the above-described HAse assay. Degradation of HA is correlated with the presence of aaHAse in the sample which in turn is correlated with the presence of an anti-native aaHAse antibody. The general characteristics of antibodies of the invention are described below.

Antibody/Antigen Binding Forces

The forces that hold an antigen and antibody together can be classified into four general areas: (1) electrostatic; (2) hydrogen bonding; (3) hydrophobic; and (4) Van der Waals. Electrostatic forces are due to the attraction between oppositely charged ionic groups on two protein side-chains. The force of attraction (F) is inversely proportional to the square of the distance (d) between the charges. Hydrogen bonding forces are due to formation of reversible hydrogen bridges between hydrophilic groups such as —OH, —NH, and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalanine tend to associate in an aqueous environment. Lastly, Van der Waals are forces created between molecules by interaction between the external electron clouds. Further information about the different types of forces is known in the art (see, e.g., *Essential Immunology*, I. M. Roitt, ed., 6th Ed. Blackwell Scientific Publications, 1988.

Useful antibodies of the present invention exhibit all of these forces. By obtaining an accumulation of these forces in greater amounts, it is possible to obtain an antibody that has a high degree of affinity or binding strength to native aaHAse, and in particular an antibody that has a high degree of binding strength to aaHAse in the material in which it naturally occurs (e.g., human plasma).

Measuring Antibody/Antigen Binding Strength

The binding affinity between an antibody and an antigen ia an accumulative measurement of all of the forces described above. Standard procedures for carrying out such measurements are known in the art and can be directly applied to measure the affinity of anti-native aaHAse antibodies of the invention.

One standard method for measuring antibody/antigen binding affinity uses a dialysis sac, composed of a material permeable to the antigen but impermeable to the antibody. Antigens that bind completely or partially to antibodies are placed within the dialysis sac in a solvent (e.g., water). The sac is then placed within a larger container which does not contain antibodies or antigen but contains only the solvent. Since only the antigen can diffuse through the dialysis membrane the concentration of the antigen within the dialysis sac and the concentration of the antigen within the outer larger container will attempt to reach an equilibrium. The amount of antigen that remains bound to antibody in the dialysis sac and the amount that disassociated from the antibody are calculated by determining the antigen concentrations within the dialysis sac and within the solvent outside the dialysis sac. By constantly renewing the solvent (e.g., the water) within the surrounding container so as to remove any diffused antigen, it is possible to totally disassociate the antibody from antigen within the dialysis sac. If the surrounding solvent is not renewed, the system will reach an equilibrium, and the equilibrium constant (K) of the reaction, i.e., the association and disassociation between the antibody and antigen, can be calculated. The equilibrium constant (K) is calculated as an amount equal to the concentration of antibody bound to antigen within the dialysis sac divided by the concentration of free antibody combining sites times the concentration of free antigen. The equilibrium constant or "K" value is generally measured in terms of liters per mole. The K value is a measure of the difference in free energy ($\Delta G$) between the antigen and antibody in the free state as compared with the complexed form of the antigen and antibody. Anti-native aaHAse antibodies having an affinity or K value of $10^7$ l/mole to $10^9$ l/mole or more are preferred.

Antibody Avidity

As indicated above the term "affinity" describes the binding of an antibody to a single antigen determinate. The term "avidity" is used to express the interaction of an antibody with a multivalent antigen. The factors that contribute to avidity are complex and include both the heterogeneity of the antibodies in a given serum that are directed against each determinate on the antigen and the heterogeneity of the determinants themselves. The multivalence of most antigens leads to an interesting "bonus" effect in which the binding of two antigen molecules by an antibody is always greater, usually many fold greater, than the arithmetic sum of the individual antibody links. Thus, it can be understood that the measured avidity between an antiserum and a multivalent antigen will be somewhat greater than the affinity between an antibody and a single antigen determinate.

Uses of Anti-Native aaHAse Antibodies

Anti-native aaHAse antibodies are useful in various immunotechniques, including immunopurification and immunodetection techniques. Anti-native aaHAse antibodies useful in such immunotechniques may be either polyclonal or monoclonal antibodies, preferably monoclonal antibodies.

Preferably, anti-native aaHAse antibodies useful in immunotechniques exhibit an equilibrium or affinity constant ($K_d$) of at least $10^7$ l/mole to $10^9$ l/mole or greater. The binding affinity of $10^7$ l/mole or more may be due to (1) a single monoclonal antibody (i.e., large numbers of one kind of antibody) (2) a plurality of different monoclonal antibodies (e.g., large numbers of each of five different monoclonal antibodies) or (3) large numbers of polyclonal antibodies. It is also possible to use combinations or (1)-(3).

Preferred antibodies bind 50% or more of native aaHAse in a sample. However, this may be accomplished by using several different antibodies as per (1)-(3) above. An increased number of different antibodies is generally more effective than a single antibody in binding a larger percentage of antigen in a sample. Thus, a synergistic effect can be obtained by combining combinations of two or more antibodies which bind native aaHAse, i.e., by combining two or more antibodies that have a binding affinity $K_a$ for native aaHAse of $10^7$ l/mole or more.

Immunopurification Using Anti-Native aaHAse Antibodies

Anti-native aaHAse antibodies can be used in, for example, immunopurification of aaHAse from its naturally occurring source (e.g., hpHAse from human blood, plasma, serum, or urine) or from a source of recombinant aaHAse production (e.g., from supernatants or cell lysates of transformed cells expressing hpHAse). Immunopurification techniques useful with the anti-native aaHAse antibodies of the invention include, but are not limited to, immunoprecipitation, immunoaffinity isolation on beads, immunoaffinity column chromatography, and other methods well known in the art. Anti-native aaHAse antibodies useful in immunopurification techniques The immunopurification methods using the antibodies of the invention can use a single anti-native aaHAse antibody (e.g, a monoclonal or polyclonal antibody, preferably a monoclonal antibody) or multiple anti-native aaHAse antibodies.

In addition, the anti-native aaHAse antibodies of the invention can be used to prepare a device for immunopurification of native aaHAse, preferably native hpHAse. In general, such devices are prepared by covalently binding an anti-native aaHAse antibody to an insoluble support (e.g., bead, affinity column component (e.g., resin), or other insoluble support used in immunoaffinity purification). Alternatively, the antibody may be bound to a metal particle which allows separation of anti-native aaHAse-aaHAse complexes from a solution by use of a magnetized column. The anti-aaHAse antibody may be a monoclonal or polyclonal antibody, preferably a monoclonal antibody. The antibodies bound to the insoluble support (or otherwise employed in purification) may also comprise a mixture of anti-native aaHAse antibodies to provide a device that can bind to at least 50% of the native aaHAse in the sample. Such immunopurification devices can be used to isolate aaHAse from a source in which it naturally occurs (e.g., hpHAse from raw serum, raw plasma, or urine) or from a source of recombinantly-produced aaHAse.

Qualitative and Quantitative Immunodetection Using Anti-Native aaHAse Antibodies Anti-native aaHAse antibodies can be used in immunodetection assay to detect and, where desirable, quantitate aaHAse in a sample. Immunodetection assays using anti-native aaHAse antibodies can be designed in a variety of ways. For example, anti-native aaHAse antibodies can be used to produce an assay device comprising anti-native aaHAse antibodies bound to a soluble support (e.g., an immunoassay column, beads, or wells of a microtiter plate). Methods for covalent or non-covalent attachment of an antibody to a soluble support are well known in the art. A sample suspected of containing an aaHAse is then contacted with the assay device to allow formation of anti-native aaHAse antibody-aaHAse complexes. The anti-native aaHAse-aaHAse complexes can then be detected by virtue of an aaHAse activity associated with the complex as described in the anti-native aaHAse assay described above, or by contacting the complex with a second detectably-labeled anti-native aaHAse antibody.

By "detectably labeled antibody", "detectably labeled anti-aaHAse" or "detectably labeled anti-aaHAse fragment" is meant an antibody (or antibody fragment that retains antigen binding specificity), having an attached detectable label. The detectable label is normally attached by chemical conjugation; where the label is a polypeptide, the label can be attached by genetic engineering techniques. Detectable labels may be selected from a variety of such labels known in the art, but normally are radioisotopes, fluorophores, paramagnetic labels, enzymes (e.g., horseradish peroxidase), or other moieties or compounds that either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin)), methods for labelling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.)).

Alternatively, detectably labeled anti-native aaHAse antibodies can be directly used to detect and/or quantify aaHAse in a sample. For example, detectably labeled anti-native aaHAse antibodies can be contacted with a tissue sample suspected of having a LuCa-1/hpHAse defect (e.g., a tissue sample derived from breast, ovaries, or lung) for a time sufficient to allow for formation of complexes between the anti-native hpHAse antibody and hpHAse in the tissue sample (e.g., hpHAse in the plasma membrane of cells of the tissue sample). Binding of the anti-native hpHAse antibody can then be detected and/or quantified by virtue of a detectable label bound to the anti-native hpHAse antibody. Alternatively, binding of the anti-native hpHAse antibody can be detected using an antibody that binds the anti-native hpHAse antibody. Binding of anti-native hpHAse antibody to a tissue sample can then be compared to anti-native hpHAse antibody binding to a control sample (e.g., a normal sample having no LuCa-1/hpHAse defect and/or a sample containing tissue associated with a LuCa-1/hpHAse defect) and the antibody binding correlated with the presence or absence of a LuCa-1/hpHAse defect in the patient.

The aaHAse immunodetection assays can be used in a variety of different ways with a variety of samples, as will be apparent to one of ordinary skill in the art upon reading the disclosure provided herein. For example, the aaHAse immunodetection assays can be used to detect hpHAse in serum or plasma samples of patient receiving hpHAse therapy and/or to correlate hpHAse in the serum or plasma of a patient with tumor progression in the patient, responsiveness to therapy, and/or uptake of hpHAse by the patient's body.

Where hpHAse is detected in serum or urine, the levels of hpHAse can be correlated with susceptibility to and/or the presence of a LuCa-1 defect associated disease state and/or the severity of such disease For example, hpHAse levels in patients having lung cancer associated with a heterozygous defect in LuCa-1 are approximately 50% of normal hpHAse levels, while patients having a homozygous defect in LuCa-1 exhibit hpHAse levels that are very low or undetectable. Thus, hpHAse levels, as detected in an aaHAse assay of the invention or detected using an anti-native hpHAse antibody of the invention, can not only be correlated with tumor progression, but can also be directly correlated with a genetic defect in LuCa-1, thus allowing identification of patients susceptible to conditions associated with LuCa-1 defects, e.g., cancer. Thus, the present invention allows one to directly correlate hpHAse levels with the number of functional alleles in a patient and to detect a genetic defect by simply ascertaining the level of hpHAse in blood, plasma, serum or urine.

Methods of Making hpHAse

In addition to the purification procedure outlined above, hpHAse hyaluronidase polypeptides can be made by standard synthetic techniques, or by using recombinant DNA technology and expressed in bacterial, yeast, or mammalian cells using standard techniques. As used herein, the term "hpHAse" includes natural, recombinant, and modified forms of the protein unless the context in which the term is used clearly indicates otherwise.

Chemical Synthesis hpHAse polypeptides can be synthesized based on the amino acid sequences described herein and variations thereof by standard solid-phase methods using the tert-butyloxy-carbonyl and benzyl protection strategy described in Clark-Lewis et al., *P.N.A.S., USA*, 90:3574-3577 (1993) and Clark-Lewis et al., *Biochemistry*, 30:3128-3135 (1991). After deprotection with hydrogen fluoride, the proteins are folded by air oxidation and purified by reverse-phase HPLC. Purity is determined by reverse-phase HPLC and isoelectric focusing. Amino acid incorporation is monitored during synthesis, and the final composition is determined by amino acid analysis. The correct covalent structure of the protein can be confirmed using ion-spray mass spectrometry (SCIEX APIII).

Recombinant DNA Techniques for Synthesis of hpHAse Polypeptides

As discussed in the examples below, LuCa-1 and hpHAse are identical. The only variation between the partial amino acid sequence of hpHAse and the amino acid sequence of LuCa-1 is a substitution of Val for Leu in the N-terminus at the 27th amino acid residue (where the Met at the N-terminus of the signal sequence is counted as the first amino acid residue); however, the two proteins are otherwise identical in amino acid sequence and immunological and biochemical characteristics. The nucleotide sequence encoding hpHAse is identical to the sequence encoding LuCa-1, except that the cytosine of the third residue in the codon corresponding to the 27th amino acid residue (Leu in LuCa-1; Val in HpHAse) is substituted with guanine. Thus, the nucleotide sequence encoding LuCa-1 is the nucleotide sequence encoding hpHAse. The LuCa-1/hpHAse gene has been isolated and sequenced (Bader et al. GenBank accession no. U03056, NID G532973, submitted Nov. 1, 1993; see also GenBank Accession No. U96078). The amino acid and nucleotide sequences of LuCa-1 as described by Bader et al. are provided below.

(SEQ ID NO: 3)
MAGHLLPICALFLTLLDMAQGFRGPLVPNRPFTTVWNANTQWCLERHGVDV
DVSVFDVVANPGQTFRGPDMTIFYSSQLGTYPYYTPGEPVFGGLPQNASLI
AHLARTFQDILAAIPAPDFSGLAVIDWEAWRPRWAFNWDTKDIYRQRSRAL
VQAQHPDWPAPQVEAVAQDQFQGAARAWMAGTLQLGGALRPRGLWGFYGFP

-continued

DCYNYDFLSPNYTGQCPSGIRAQNDQLGWLWGQSRALYPSIYMPAVLEGTG
KSQMYVQHRVAEAFRVAVAAGDPNLPVLPYVQIFYDTTNIFLPLDELEHSL
GESAAQGAAGVVLWVSWENTRTKESCQAIKEYMDTTLGPFILNVTSGALLC
SQALCSGHGRCVRRTSHPKALLLLNPASFSIQLTPGGGPLSLRGALSLEDQ
AQMAVEFKCRCYPGWQAPWCERKSMW (SEQ ID NO: 4)
```
   1 ttcctccagg agtctctggt gcagctgggg tggaatctgg ccaggccctg cttaggcccc
  61 catcctgggg tcaggaaatt tggaggataa ggcccttcag ccccaaggtc agcagggacg
 121 agcgggcaga ctggcgggtg tacaggaggg ctgggttgac ctgtccttgg tcactgaggc
 181 cattggatct tcctccagtg gctgccagga tttctggtgg aagagacagg aaggcctccc
 241 ccccatggtc gggtcagcct gggggctgag ggcctggctg tcagccactc ttcccagaac
 301 atatgtcatg gcctcagtgg ctcatgggga agcaggggtg ggcgagctta ggctagagca
 361 agtcctgtgg gagatggcag aggcctggtc tgagaggcaa ctcggatgtg ccctccagtg
 421 gccatgctcc cctccatgcg tctcccclgc cctccggag ccctgcaggt caatgtttaa
 481 cagaaaccag agcagcggig gattaatgcg caagggctca gcccccagc cctgagcagt
 541 ggggaatcg gagactttgc aacctgttct cagctctgcc tcccctgggc aggttgtcct
 601 cgaccagtcc cgtgccatgg caggccacct gcttcccatc tgcgccctct tcctgacctt
 661 actcgatatg gcccaaggct ttaggggccc cttggtaccc aaccgccct tcaccaccgt
 721 ctggaatgca aacacccagt ggtgcctgga gaggcacggt gtggacgtgg atgtcagtgt
 781 cttcgatgtg gtagccaacc cagggcagac cttccgcggc cctgacatga caattttcta
 841 tagctcccag ctgggcacct accctacta cacgcccact ggggagcctg tgtttggtgg
 901 tctgccccag aatgccagcc tgattgccca cctggcccgc acattccagg acatcctggc
 961 tgccatacct gctcctgact tctcagggct ggcagtcatc gactgggagg catggcgccc
1021 acgctgggcc ttcaactggg acaccaagga catttaccgg cagcgctcac gggcactggt
1081 acaggcacag caccctgatt ggccagctcc tcaggtggag cagtagccc aggaccagtt
1141 ccagggagct gcacgggcct ggatggcagg caccctccag ctgggggggg cactgcgtcc
1201 tcgcggcctc tggggcttct atggcttccc tgactgctac aactatgact ttctaagccc
1261 caactcacc ggccagtgcc catcaggcat ccgtgcccaa aatgaccagc tagggtggct
1321 gtggggccag agccgtgccc tctatccag catctacatg cccgcagtgc tggagggcac
1381 agggaagtca cagatgtatg tgcaacaccg tgtggccgag gcattccgtg tggctgtggc
1441 tgctggtgac cccaatctgc cggtgctgcc ctatgtccag atcttctatg acacgacaaa
1501 ccactttctg ccctggaig agctggagca cagcctgggg gagagtgcgg cccaggggc
1561 agctggagig gtgctctggg tgagctggga aaatacaaga accaaggaat catgtcaggc
1621 catcaaggag tatatggaca ctacactggg gcccticatc ctgaacgtga ccagtggggc
1681 ccttctctgc agtcaagccc tgtgctccgg ccatggccgt gtgtccgcc gcaccagcca
1741 ccccaaagcc ctcctcctcc ttaaccctgc cagtttctcc atccagctca cgcctggtgg
1801 tggcccctg agcctgcggg gtgccctctc acttgaagat caggcacaga tggctgtgga
1861 gttcaaatgt cgatgctacc ctggctgca ggcaccgtgg tgtgagcgga agagcatgtg
1921 gtgattggcc acacactgag ttgcacatat tgagaaccta atgcactctg gtctggcca
```

```
-continued 1981  gggcttcctc  aaatacatgc  acagtcatac  aagtcatggt  cacagtaaag  agtacactca 2041  gccactgtca  caggcatatt  ccctgcacac  acatgcatac  ttacagactg  gaatagtggc 2101  ataaggagtt  agaaccacag  cagacaccat  tcattcctgc  tccatatgca  tctacttggc 2161  aaggtcatag  acaattcctc  cagagacact  gagccagtct  ffgaactgca  gcaatcacaa 2221  aggctgacat  tcactgagtg  cctactcttt  gccaatcccc  gtgctaagcg  ttttatgtgg 2281  acttattcat  tcctcacaat  gaggctatga  ggaaactgag  tcactcacat  tgagagtaag 2341  cacgttgccc  aaggttgcac  agcaagaaaa  gggagaagtt  gagattcaaa  cccaggctgt 2401  ctagctccgg  gggtacagcc  cttgcactcc  tactgagttt  gtggtaacca  gccctgcacg 2461  acccctgaat  ctgctgagag  gcaccagtcc  agcaaataaa  gcagtcatga  tttactt
```

The nucleotide sequence encoding hpHAse can be isolated according to any one of a variety of methods well known to those of ordinary skill in the art. For example, DNA encoding hpHAse can be isolated from either a cDNA library or from a genomic DNA library by hybridization methods. Alternatively, the DNA can be isolated using standard polymerase chain reaction (PCR) amplification of synthetic oligonucleotide primers, e.g., as described in Mullis et al., U.S. Pat. No. 4,800,159, or expression cloning methods well known in the art (see, e.g., Sambrook et al. Sambrook et al. 1989 *Molecular Cloning: A Laboratory Manual*, 2nd Ed., Cold Spring Harbor Laboratory Press, Cold Spring Harbor, N.Y.). Where hybridization or PCR is used to identify DNA encoding hpHAse, the sequence of the oligonucleotide probes or primers can be based upon the amino acid or nucleotide sequence of LuCa-1 provided above. The sequence of isolated hpHAse polypeptide-encoding DNA can be determined using methods well known in the art (see, for example, Sambrook et al., supra). Following sequence confirmation, the resulting clones can be used to for example, identify homologs of a hpHAse (e.g., other human alleles encoding hpHAse or an acid active serum hyaluronidase of another mammalian species (e.g., dog, rat, mouse, primate, cow), and/or to transform a target cell in a host for expression of the hpHAse-encoding DNA (e.g., as in anti-cancer therapy through hpHAse polypeptide expression in host cells, preferably cancerous cells of a patient).

Production of hpHAse-Encoding Constructs and Expression of hpHAse Polypeptides

Numerous vectors are available for production of hpHAse-encoding constructs and hpHAse expression (see, e.g., the American Type Culture Collection, Rockville, Md.). Preferably the vector is capable of replication in both eukaryotic and prokaryotic hosts, and are generally composed of a bacterial origin of replication and a eukaryotic promoter operably linked to a DNA of interest, thereby allowing production of hpHAse-encoding constructs. Suitable host cells, as well as methods for constructing stably-transformed host cell lines, are also publicly available, e.g., Pouwels et al., 1985, *Cloning Vectors: A Laboratory Manual*, Ausubel et al., 1989, *Current Protocols in Molecular Biology*, John Wiley & Sons, New York; Sambrook et al., supra; Kormal et al., 1987, *Proc. Natl. Acad. Sci. USA*, 84:2150-2154; each of which are hereby incorporated by reference with respect to methods and compositions for manipulation of a DNA of interest).

Expression of an hpHAse polypeptide is accomplished by inserting a nucleotide sequence encoding an hpHAse polypeptide into a nucleic acid vector such that a promoter in the construct is operably linked to the hpHAse-encoding sequence, which construct is then used to transform a host cell. hpHAse expression can be accomplished in a mammalian cell line by either transient, constitutive, or inducible expression. In one preferred embodiment, the host cell is a mammalian cell, preferably a cos-7 cell line, or a cos-7 cell-derived cell line. More preferably, the host cell for hpHAse production is a mammalian cell that is protected against hpHAse expression (i.e., the cell can produce high levels of hpHAse without adverse affects upon the host cell (e.g., slow cell growth, cell death)). In one embodiment, the hpHAse-resistant cell is an SV-transformed cell line or an adenovirus-transformed cell line (i.e., a cell line transformed with sheared adenovirus), preferably the HEK cell line (HEK 293) For example, transformation of HEK cells with hpHAse-encoding DNA driven by a strong promoter (e.g., CMV) provides surprisingly high hpHAse expression and secretion into the culture medium (approximately $2.9 \times 10^{-10}$ mg/cell/24 hrs.) (>100 rTRU). Use of such cell lines allows for production of sufficient quantities of hpHAse for use in, e.g, protein therapy.

Where expression is desired in a tumor cell line that is not resistant to hpHAse, the hpHAse-encoding DNA is preferably under control of an inducible promoter, preferably an inducible promoter responsive to an inducing agent that does not significantly affect other mammalian cells in the vicinity of the transformed, hpHAse construct-containing cells. For example, the hpHAse-encoding DNA can be under the control of a steroid inducible promoter (e.g., in the ecdysone expression system, which is inducible by muristerone). The target cells are transformed and, upon exposure to the inducing agent, express hpHAse.

Where the hpHAse-encoding DNA is used to transform tumor cells for treatment of a tumor-bearing patient, the hpHAse-encoding DNA may be transiently, constitutively, or inducibly expressed, preferably transiently or constitutively expressed, more preferably constitutively expressed. In addition or alternatively, peritumor cells (e.g., cells adjacent the tumor cells) or other cells capable of expressing and secreting hpHAse (e.g., liver cell or monocyte) can be transformed.

Recombinant hpHAse polypeptide expression (e.g., produced by any of the expression systems described herein) can be assayed by immunological procedures, such as Western blot or immunoprecipitation analysis of recombinant cell extracts, or by the HAse activity assay of the invention as described herein. For example, hpHAse polypeptides according to the invention can be produced by transformation of a suitable host cell with an hpHAse polypeptide-encoding nucleotide sequence in a suitable expression vehicle, and culturing the transformed cells under conditions that promote expression of the encoded polypeptide, and preferably secretion of hpHAse into the culture medium. The method of transformation and the choice of expression vehicle will depend on the host system selected. Those skilled in the field of molecular biology will understand that any of a wide variety of prokaryotic and eukaryotic expression systems may be used to produce hpHAse polypeptides of the invention.

Identification of Biologically Active hpHAse Polypeptides hpHAse polypeptide-encoding DNAs can encode all or a portion of an hpHAse. Preferably, the hpHAse polypeptide is biologically active, e.g., exhibits acid active hyaluronidase activity in the cleavage of hyaluronan and/or can be bound by an anti-native hpHAse antibody. In general, once information regarding the ability of a protein to elicit antibodies and/or information regarding an enzymatic or other biological activity of a protein of interest is known, methods for identification of biologically active polypeptides of the full-length protein are routine to the ordinarily skilled artisan, particularly where the nucleotide sequence and/or amino acid sequence encoding the protein of interest (here hpHAse) is provided as in the present case.

Biologically active hpHAse polypeptides can be identified by using the HAse activity assay of the invention, or by using conventional HAse activity assays (e.g., the ELISA-like hyaluronan assay (Stem et al., 1992, *Matrix* 12:391-403) or substrate gel zymography (Guentenhoener et al., 1992, *Matrix* 12:388-396)). Alternatively, biologically active hpHAse polypeptides can be detected by binding of an anti-native hpHAse antibody to a component of the transformed host cell supernatant and/or lysate. hpHAse polypeptides preferably exhibit at least 25%, more preferably 50%, still more preferably 75%, even more preferably 95% of the activity of native hpHAse.

Identification of Hyaluronidases Homologous to hpHAse

DNA encoding hyaluronidases homologous to hpHAse (e.g., contain conservative amino acid substitutions relative to a native hpHAse) can be accomplished by screening various cDNA or genomic DNA libraries by hybridization or PCR using oligonucleotides based upon the DNA sequence and/or amino acid sequence of an hpHAse (e.g., a LuCa-1/hpHAse sequence). Alternatively the oligonucleotides used may be degenerate, e.g., based upon a selected amino acid sequence of hpHAse or designed so as to allow detection or amplification of DNA encoding an hpHAse-like amino acid sequence having conservative amino acid substitutions and/or to take into account the frequency of codon usage in the mammalian species DNA to be screened. Such "degenerate oligonucleotide probes" can be used in combination in order to increase the sensitivity of the hybridization screen, and to identify and isolate hpHAse analogs in other species or variant alleles encoding hpHAse in humans. Methods for designing and using degenerate oligonucleotide probes to identify a protein for which an amino acid and/or nucleotide sequence, as well as methods for hybridization and PCR techniques for screening and isolation of homologous DNAs, are routine and well known in the art (see, for example, Sambrook et al. supra).

Alternatively, the DNA encoding hpHAse may be isolated by expression cloning methods well known in the art (see, for example, Sambrook et al., supra). For example, mammalian cells can be transformed with a cDNA expression library, i.e., a collection of clones containing various cDNA fragments operably linked to a eukaryotic promoter. Expression of an hpHAse homology or a biologically active fragment thereof can be detected by assaying the culture supernatant and/or cell lysates using the HAse activity assay of the invention.

Therapies Using hpHAse Polypeptides

The substantially pure native hpHAse polypeptides (e.g., hpHAse polypeptides that are not associated with the components of plasma from which hpHAse is purified) of the invention can be used in a variety of applications including human and veterinary therapies, either alone or in combination with other therapeutic agents. Purified hpHAse of the invention can generally be used in place of neutral HAse formulations or WYDASE™ bovine testicular hyaluronidase, where the condition to be treated is associated with excess hyaluronic acid and/or therapy is designed to increase HAse activity generally (i.e., the conventional neutral hyaluronidase-containing formulation is not used to treat a specific defect in neutral HAse activity, but rather provides a HAse (neutral or acid active) activity). Use of acid active hpHAse is preferred to use of neutral HAses since acid active hpHAse can provide controlled degradation of HA substrate and does not degrade all components of the extracellular matrix in the patient.

hpHAse can be used in the treatment of diseases associated with excess hyaluron, to enhance circulation of physiological fluids at the site of administration (e.g., as a spreading agent, e.g., by subcutaneous or topical application (e.g., in cosmetic formulations such as cosmetic creams), and/or as an anti-cancer agent either alone or in combination with chemotherapeutic agents. For example, hpHAse can be administered to a patient to facilitate clysis, particularly hypodermoclysis. hpHAse can also be administered to patients suffering from stroke or a myocardial infarction (e.g., by infusion). Preferably, hpHAse is administered in the absence, or at very low levels, of heparin, a powerful inhibitor of hyaluronidase. Methods for administration, and amounts of hpHAse administered, for treatment of myocardial infarction can be based upon methods of administration of bovine testicular hyaluronidase and amounts administered (see, e.g., Wolf et al. 1982 *J. Pharmacol. Exper. Therap.* 222:331-7; Braunwald et al. 1976 *Am. J. Cardiol.* 37:550-6; DeGiovanni et al. 1961 *Br. Heart J.* 45:350; DeOliveira et al. 1959 *Am. Heart J.* 57:712-22; Kloner et al. 1978 *Circulation* 5:220-6; Kloner et al. 1977 *Am. J. Cardiol.* 0:43-9; Koven et al. 1975 *J. Trauma* 15:992-8; Maclean et al. 1978 *J. Cin. Invest.* 61:541-51; Maclean et al. 1976 *Science* 194:199-200; Maroko et al. 1975 *Ann. Intern. Med.* 82:516-20; Maroko et al. 1977 *N. Engl. J. Med.* 296:896-903; Maroko et al. 1972 *Circulation* 46:430-7; Salete 1980 *Clin. Biochem.* 13:92-94; Snell et al. 1971 *J. Clin. Invest.* 50:2614-25; Wolf et al. 1981 *Circ. Res.* 48:88-95).

Furthermore, hpHAse can also have therapeutic effects when administered to patients having certain lysosomal storage diseases associated with a defect in hyaturonidase (see, e.g., Natowicz et al. 1996 *N. Engl. J. Med.* 335:1029-33). hpHAse can used therapeutically by direct administration of hyaluronidase (e.g., intracellularly or intravenously) as a form of shunt pathway and/or by gene therapy (e.g., to replace defective copy(ies) of the LuCa-1 gene). Lysosomal storage disease amenable to hpHAse therapy are those diseases that result in accumulation of $[GlcNAc\beta1\text{-}4GlcUA\beta1\text{-}3]_n$ (GAGs) due to a defective mannose-6-phosphate pathway. hpHAse can degrade these accumulated GAGs under a non-functional cellular system since HAse activity does not depend upon the mannose-6-phosphate pathway (Herd et al. 1976 *Proc. Soc. Experim. Biol. Med.* 151:642-9).

hpHAse can also be used in the treatment of edema associated with brain tumors, particularly that associated with glioblastoma multiform. The edema associated with brain tumors results from the accumulation of hyaluronan in the non-cancerous portions of the brain adjacent the tumor. Administration of hyaluronidase to the sites of hyaluronan accumulation (e.g., by intravenous injection or via a shunt) can relieve the edema associated with such malignancies by degrading the excess hyaluronan at these sites. Thus, hyaluronidase is successful in the treatment of brain tumors not only in the reduction of the tumor mass and inhibition of tumor growth and/or metastasis, but it also is useful in relieving edema associated with the malignancy. hpHAse can be administered for treatment of edema in a manner similar to that for administration of bovine testicular hyaluronidase to treat edema (see, e.g., SaEarp *Arq. Braz. Med.* 44:217-20).

Of particular interest is the use of hpHAse polypeptides in the treatment of metastatic and non-metastatic cancers, particularly metastatic cancers, having decreased to undetectable hpHAse activity relative to non-cancerous (normal) cells. hpHAse can be used as a chemotherapeutic agent (alone or in combination with other chemotherapeutics) in the treatment of any of a variety of cancers, particularly invasive tumors. For example, hpHAse polypeptides can be used in the treatment of small lung cell carcinoma, squamous lung cell carcinoma, as well as cancers of the breast, ovaries, head and neck, or any other cancer associated with depressed levels of hpHAse or with a defective LuCa-1 (hpHAse) gene (e.g., a LuCa-1 gene that does not provide for expression of adequate hpHAse levels or encodes a defective hpHAse that does not provide for an adequate level of hyaluronidase activity) or other defect associated with decreased hpHAse activity.

hpHAse can also be used to increase the sensitivity of tumors that are resistant to conventional chemotherapy. In one embodiment, hpHAse is administered to a patient having a tumor associated with a LuCa-1 defect in an amount effective to increase diffusion around the tumor site (e.g., to increase circulation of chemotherapeutic factors (e.g., to facilitate circulation and/or concentrations of chemotherapeutic agents in and around the tumor site), inhibit tumor cell motility (e.g., by HA degradation) and/or to lower the tumor cell(s) threshold of apoptosis (i.e., bring the tumor cell(s) to a state of anoikis), a state that renders the tumor cell(s) more susceptible to the action of chemotherapeutic agents or other agents that may facilitate cell death, preferably preferentially facilitate programmed cell death of cells in anoikis. Chemotherapeutic agents as used herein is meant to encompass all molecules, synthetic (e.g, cisplatin) as well as naturally-occurring (e.g., tumor necrosis factor (TNF)), that facilitate inhibition of tumor cell growth, and preferably facilitate, more preferably preferentially facilitate tumor cell death.

Patients having or susceptible to a disease or condition that is amenable to treatment with hpHAse can be identified using a variety of conventional methods, or by using an assay device of the invention having bound anti-native hpHAse antibodies as described above to determine blood, plasma, serum, or urine hpHAse levels, preferably blood, plasma, or serum, and correlate such levels with a LuCa-1 defect. For example, where the patient is suspected of having or of being susceptible to a condition associated with decreased hpHAse activity, a biological sample (e.g., blood, serum, or plasma) can be obtained from the patient and assayed using the HAse assay and/or immunoassays using anti-native hpHAse antibodies as described above.

Alternatively, particularly where the patient has or is suspected of having a cancer associated with a LuCa-1/hpHAse defect, anti-native hpHAse antibodies can be used to determine the levels of hpHAse in a tissue sample (e.g., hpHAse present in the plasma membrane of, inside of, or surrounding cells associated with the tumor tissue). Decreased levels of hpHAse in the tissue sample relative to levels of hpHAse associated with a normal (i.e., non-cancerous) tissue sample is indicative of a LuCa-1/hpHAse defect-associated cancer.

The route of administration and amount of hpHAse administered will vary widely according to the disease to be treated, and various patient variables including size, weight, age, disease severity, and responsiveness to therapy. Methods for determining the appropriate route of administration and dosage are generally determined on a case-by-case basis by the attending physician. Such determinations are routine to one of ordinary skill in the art (see, for example, *Harrison's Principles of Internal Medicine,* 11th Ed., 1987). For example, where hpHAse is used to facilitate hypodermoclysis, a solution containing hpHAse is administered by subcutaneous injection to facilitate absorption of the solution (e.g., nutrient, body fluid replacement, or blood pressure increasing solution). Preferably, hpHAse is administered by injection, e.g., parenteral injection including subcutaneous, intramuscular, intraorbital, intracapsular, peritumoral, and intravenous injection.

In a preferred embodiment, hpHAse polypeptide is delivered to the patient having an hpHAse-treatable tumor by delivery of hpHAse polypeptide directly to the tumor site, e.g., by peritumoral injection of hpHAse, injection or hpHAse directly into the tumor mass, and/or introduction of hpHAse-encoding DNA in a tumor cell, peritumor cell, or other cell capable of expressing and secreting hpHAse (e.g., liver cell or monocyte). Because hpHAse has a fatty acid modification (e.g., a lipid moiety), hpHAse may be readily incorporated into the plasma membrane of cells following injection at the site where hpHAse action is desired (see, e.g., 1995 *J. Cell Bio.* 13(3):669-77). Further, hpHAse may also complex with LDL (Low Density Lipoprotein) receptors and be internalized into the cell by receptor-mediated endocytosis.

In one preferred embodiment, hpHAse is delivered to the patient within a liposome formulation to provide intracellular delivery of hpHAse to the target cell (e.g., a cancerous cell having a LuCa-1/hpHAse defect) and/or incorporating hpHAse into the plasma membrane of such target cell. Preferably, the liposome formulation is prepared to provide for specific, targeted delivery of hpHAse incorporated within the liposome to a target cell. Because hpHAse is fairly insoluble in aqueous solution (e.g., hpHAse precipitates in aqueous solution when the NaCl concentration is less than 50 mM), liposome incorporation creates a more soluble preparation due to the biochemical characteristics of hpHAse associated with its post-translational fatty acid chain modification. Furthermore, introduction of hpHAse into the circulation would likely result in association of hpHAse with high density lipoprotein (HDL) complexes, since hpHAse co-purifies with these lipid fractions of plasma.

The biochemical characteristics identified by the present inventors indicate that hpHAse can be easily incorporated into liposomes. Methods for preparation of liposomes and administration of same are well known in the art. For example, hpHAse-containing liposomes can be prepared by combining detergent-free immunoaffinity purified (IAP) hpHAse and liposome formulation as described in *Liposome Technology,* G. Gregoriadis, ed., 1984, CRC Press, Boca Raton, Fla. Preferably the liposome formulation of the invention comprises a compound(s) that enhance hpHAse activity. In a preferred embodiment, the hpHAse liposome formulation comprises cholesterol and/or cardiolipin, more preferably, cardiolipin. Without being held to theory, cardiolipin enhances hpHAse activity by preventing the denaturation of hpHAse, thus maintaining the stability of the enzyme and enhancing its incorporation into the plasma membranes of target cells. As discovered by the inventors, hpHAse activity is not enhanced by the presence of phosphatidyl-ethanolamine or phosphatidyl-choline. Liposome formulations comprising cholesterol and cardiolipin are especially preferred.

Especially where hpHAse is to be used in therapy, e.g., chemotherapy, it may be desirable to modify hpHAse to provide one or more desirable characteristics. For example, although hpHAse is a serum protein and thus should inherently have a substantial half-life in serum, it may be desirable to increase its biological half-life (e.g., serum half-life) by, for example, modification of the polypeptide. Various methods for increasing the half-life of a protein are well known in the art and include, for example, conjugation of the protein to polyethylene glycol moieties, i.e., PEGylation (see, for example, U.S. Pat. No. 4,179,337; U.S. Pat. No. 5,166,322; U.S. Pat. No. 5,206,344; Nucci et al., 1991, *Adv. Drug Delivery Rev.* 4:133-151; Zalipsky et al., 1991, "Polymeric Drugs and Drug Delivery Systems," ACS) conjugation of the protein to dextran (Maksimenko, 1986, *Bull. Exp. Biol. Med.* (*Russian*) 52:567-569), and degtycosylation of the protein by treatment with endoglycosidase F (Lace et al., 1990, *Carbohydrate Res.* 208:306-311).

In general, these methods are designed to increase the molecular weight of the protein, decrease the sensitivity of the protein to proteinases, and/or decrease the rate of clearance of the protein from the subject to be treated. The increased half-life of modified hpHAse polypeptides decreases the amount of protein needed for an effective dosage, reduces the number and frequency of administrations required, and decreases the patient's exposure to the protein, thus decreasing the potential for allergic reactions, toxic effects, or other side effect. These characteristics of modified hpHAse polypeptides having an increased half-life also allow for long-term use of the protein with less potential for undesirable side effects related to protein immunogenicity and/or toxicity. Preferably these methods can be used so that the half-life of the protein is increased without substantially compromising the protein's biological activity. The enzymatic activity of hpHAse can be assayed by, for example, using the HAse activity assay of the invention. Methods for testing the biological half-life of a proteins are well known in the art.

The specific dosage appropriate for administration can be readily determined by one of ordinary skill in the art according to the factors discussed above (see, for example, *Harrison's Principles of Internal Medicine,* 11th Ed., 1987). In addition, the estimates for appropriate dosages in humans may be extrapolated from determinations of the level of enzymatic activity of hpHAse in vitro and/or dosages effective in animal studies. For example, 70-300 TRU hyaluronidase is effective in reducing the tumor load in a scid mouse. Given this information, the corresponding dosages in the average 70 kg human would range from about 250,000-1,200,000 TRU hyaluronidase. The amount of hpHAse polypeptide administered to a human patient is generally in the range of 1 TRU to 5,000,000 TRU of enzymatic activity, preferably between about 1,000 TRU to 2,500,000 TRU, more preferably between about 100,000 TRU to 1,500,000 TRU, normally between about 250,000 TRU and 1,200,000 TRU, with about 725,000 TRU representing average prescribed doses.

In one embodiment, an hpHAse polypeptide is formulated in a 0.15 M saline solution containing hpHAse at a concentration of about 150,000 TRU/cc. The formulation is then injected intravenously at 15,000 TRU/kg body weight of the patient. Alternatively, the enzyme formulation may also be injected subcutaneously to allow the hyaluronidase to perfuse around the tumor site. In a preferred embodiment, hpHAse is injected peritumorally or into the tumor mass. In another preferred embodiment, hpHAse is formulated as a liposome and is delivered by injection either intravenously or at or near the site of cancerous cells associated with a defect in the LuCa-1 (hpHAse) gene. Injection of hpHAse intravenously results in hpHAse in the tumor site.

Anti-Cancer Therapy by Expression of hpHAse in Cancerous or Pre-Cancerous Cells

The association of cancer with defects in the human chromosome at 3p21.3 has been described in several tissues. The LuCa-1 gene is one of several candidate tumor suppressor genes at 3p21.3. The identity of LuCa-1 and hpHAse, as well as the observations that hyaluronidase expression is associated with inhibition of tumor progression and tumor formation in mice (De Maeyer et al. supra; Pawlowski et al. supra), indicate that the LuCa-1 gene, which encodes hpHAse, has activity as a tumor suppressor gene. Therefore, introduction of a nucleotide sequence(s) encoding LuCa-1/phase into the genome of cells having a LuCa-1/phase defect can repair the defect and thus prevent or inhibit tumor development and/or progression (e.g., replacement gene therapy). The introduced hpHAse-encoding sequence can be either constitutively or inducibly expressed upon transformation of the target cell. Alternatively, the LuCa-1/phase defect can be repaired by introduction of genetic elements that may enhance expression of hpHAse (e.g., introduce an inhibitor of a factor that is responsible for inhibition of hpHAse transcription or translation). This latter approach may be useful where the hpHAse coding sequence itself is not defective, but rather the defect results from decreased expression of hpHAse. For example, transformation of tumor cells or cells in the vicinity of tumors cells (e.g., which can express hpHAse which in turn is exposed to the tumor cells) can be used in the treatment of small lung cell carcinoma, squamous lung cell carcinoma, as well as cancers of the breast, ovaries, head and neck, or any other cancer associated with depressed levels of hpHAse or with a defective LuCa-1 (phase) gene (e.g., a LuCa-1 gene that does not provide for expression of adequate hpHAse levels or encodes a defective hpHAse that does not provide for an adequate level of hyaluronidase activity) or other defect associated with decreased hpHAse activity.

Methods for introduction of a sequence of interest into a host cell to accomplish gene therapy are known in the art. In general, such gene therapy methods include ex vivo and in vivo methods. Ex vivo gene therapy according to the present invention involves, for example, transformation of cells isolated from the patient with an hpHAse polypeptide encoding sequence, and implantation of the transformed cells in the patient to provide a reservoir of hpHAse production, preferably at a site within or near the tumor. The implanted cells thus provide secreted hpHAse to combat the progression of tumor(s) in the patient. Methods for accomplishing ex vivo gene therapy are well known in the art (see, e.g., Morgan et al. 1987 *Science* 237:1476; Gerrard et al. 1993 *Nat. Genet.* 3:180). In vivo gene therapy according to the present invention is used accomplished repair of the hpHAse defect within the patient by delivery of hpHAse polypeptide-encoding nucleic acid, introduction of the nucleic acid into the cells (e.g., into cancerous cells, pre-cancerous cells, peritumoral cells, or cells capable of expressing and secreting hpHAse, preferably into cancerous or pre-cancerous cells), and expression of hpHAse by the transformed cells in the patient, thereby repairing the hpHAse defect.

Several different methods for transforming cells can be used in accordance with either the ex vivo or in vivo transfection procedures. For example, various mechanical methods can be used to deliver the genetic material, including the use of fusogenic lipid vesicles (liposomes incorporating cationic lipids such as lipofection; see Felgner et al., *Proc. Natl.*

Acad. Sci. U.S.A. 84:7413-7417 (1987)); direct injection of DNA (Wolff, et al., *Science* (1990) 247:1465-1468); pneumatic delivery of DNA-coated gold particles with a device referred to as the gene gun (Yang et al., *Proc. Natl. Acad. Sci. U.S.A.* 1990; 87:1568-9572); and various viral vectors (e.g., non-replicative mutants/variants of adenovirus, retrovirus, adeno-associated virus, herpes simplex virus (HSV), cytomegalovirus (CMV), vaccinia virus, and poliovirus). A review of the different techniques along with a citation of numerous publications in each area is contained within a recent article on human gene therapy (see Morsy et al. 1993 *JAMA* 270: 2338-2345).

The formulation to accomplish gene therapy will vary with the gene therapy method used, the route of administration (e.g., administration for systemic gene therapy or administration for transformation of specifically targeted cells), and the site targeted for transformation (e.g., lung, breast, or ovaries). The hpHAse polypeptide-encoding nucleic acid sequence may be naked (i.e., not encapsulated), provided as a formulation of DNA and cationic compounds (e.g., dextran sulfate), or may be contained within liposomes. Alternatively, the DNA of interest can be pneumatically delivered using a "gene gun" and associated techniques which are well known in the art (Fynan et al. 1993 *Proc. Natl. Acad. Sci. USA* 90:11478-11482). The various elements of the construct for hpHAse expression in the target cell (e.g., the promoter selected, the presence of elements to enhance expression) will also vary according to the cell type and level of hpHAse expression desired.

The amount of DNA administered will vary greatly according to a number of factors including the susceptibility of the target cells to transformation, the size and weight of the subject, the levels of hpHAse expression desired, and the condition to be treated. For example, the amount of DNA injected into a human breast tumor is generally from about 1 μg to 200 mg, preferably from about 100 μg to 100 mg, more preferably from about 500 μg to 50 mg, most preferably about 10 mg. Generally, the amounts of DNA for human gene therapy can be extrapolated from the amounts of DNA effective for gene therapy in an animal model. For example, the amount of DNA for gene therapy in a human is roughly 100 times the amount of DNA effective in gene therapy in a rat. The amount of DNA necessary to accomplish cell transformation will decrease with an increase in the efficiency of the transformation method used.

Numerous other uses for phase, anti-phase antibodies, and hpHAse polypeptide-encoding nucleotide sequences are readily apparent to one of ordinary skill in the art. Nucleotide sequences encoding hpHAse polypeptides can be used in hybridization screening methods to detect other hyaluronidases having homology to hpHAse.

Deposits

The hybridoma cell lines 17E9 and 4D5, which produces an anti-hpHAse antibody that binds native hpHAse, has been deposited on behalf of The Regents of the University of California, 300 Lakeside Drive, 22nd Floor, Oakland, Calif. 94612 with the American Type Culture Collection (ATCC), Rockville, Md., U.S.A. for patent purposes. The deposit of the hybridoma cell line 17E9 was received by the ATCC on Oct. 17, 1996, ATCC Designation ATCC HB-12213. The deposit of the hybridoma cell line 4D5 was received by the ATCC on Oct. 17, 1996, ATCC Designation ATCC HB-12214. The hybridoma cells were deposited under the conditions specified by the Budapest Treaty on the international recognition of the deposit of microorganisms (Budapest Treaty).

Availability of the deposited material is not to be construed as a license to practice the invention in contravention of the rights granted under the authority of any government in accordance with its patent laws.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Hyaluronidase (HAse) Activity-Assay Using Covalently-Bound Biotinylated Hyaluronic Acid Human umbilical cord hyaluronic acid (HA; ICN) was biotinylated through free carboxyl groups with biotin hydrazide (Pierce), coupled using 1-ethyl-dimethylaminopropyl carbodiamide (EDC, Sigma). 100 mg of hyaluronic acid (HA) was dissolved in 0.1 M Mes pH 5.0, and biotin hydrazide (Pierce), dissolved in DMSO, was added to a final concentration of 1 mM. EDC was dissolved into the HA/biotin solution to a final concentration of 0.03 mM and left stirring overnight at 4° C. Uncoupled biotin was then removed through exhaustive dialysis against distilled water (dH20) and was stored at −20° C. at a final concentration of 1 mg/ml.

Up to about 10 days before performing the hyaluronidase assay, the biotinylated hyaluronic acid (bHA) was then covalently coupled to Covalink-NH microtiter plates (NSNC, Placerville, N.J.) at a final concentration of 5 μg of bHA/well with 9.2 μg/well Sulfo-NHS (Pierce) and 6 μg/well fresh EDC overnight at 4° C. Unbound HA was removed through washing plates with wash buffer (PBS with 2 M NaCl, 50 mM $MgSO_4$, 0.05% Tween-20). Incubations for plasma hyaluronidase activity were performed by diluting human plasma 1:400 in assay buffer (0.1 M Formate pH 3.7, 0.1 M NaCl, 1% Triton X-100, 0.02% Azide, 5 mM CaCl2 and 5 mM sacharrolactone (to inhibit exoglycosidase activity)) and incubating 100 μl samples in the bHA plates for 30 min at 37° C. The reaction was terminated through the addition of 6 M Guanidine HCl and washed three times with PBS wash buffer.

Residual undigested hyaluronic acid remaining covalently bound to the plate was reacted with avidin peroxidase (ABC-kit Vectastain) using o-phenylendiamine as a substrate. Fluorescence associated with bHA was detected using a microtiterplate reader at 492 nm. A standard curve was generated through co-incubation of serial dilutions of bovine testicular hyaluronidase (WYDASE™) and activity of unknown samples were interpolated through a four parameter curve fit to yield values given in relative Turbidity Reducing Units (rTRU)/ml related to the standardized commercial preparations of hyaluronidase.

The bHA hyaluronidase activity assay is approximately 1,000 times more sensitive than the conventional calorimetric assay (Afify et al. supra) and requires only 60 min to complete. Moreover, the assay does not require the tedious preparation of a biotinylated-HA binding aggrecan peptide from bovine nasal cartilage as used in conventional ELISA-like assays (Stem et al. supra; Delpech et al. supra). The assay can also be used to detect HAse activity from cell cutures that produce very low levels of activity by using longer incubation periods.

Example 2

Purification of Human Plasma Hyaluronidase Using the Biochemical Purification Method of the Invention hpHAse was purified in a three-step biochemical procedure: 1) temperature-induced detergent hpHAse extraction of human plasma; 2) Fast Flow-S cation exchange chromatography; and 3) hydroxyl-apatite resin. Hyaluronidase activity and protein concentration were determined at each stage of purification, and the specific hyaluronidase activity calculated. Hyaluronidase activity was determined using the assay in Example 1. Protein concentration was determined by both absorbance at 280 nm and with the Biorad (Burlingame, Calif.) protein microassay kit (Tengblad 1979 *Biochim. Biophys. Acta* 578:281-289) in 96 well plates, using crystallized bovine serum albumin as a standard and read at 595 nM.

2) Fast Flow-S Cation Exchange Chromatography

The final detergent-rich phase from step 1) was diluted six-fold with 20 ml of equilibrated SP-Sepharose cation exchange resin (Pharmacia) in 25 mM Mes, pH 6.0 and stirred overnight at 4° C. The beads were collected through centrifugation and washed extensively with 25 mM Mes, pH 6.0, containing 46 mm octylglucoside (Boehringer Mannheim). Hyaluronidase was eluted from the beads through the addition of 0.3 M NaCl in Mes pH 6.0 buffer with several washes. The SP-Sepharose eluant was concentrated on a YM3 (Amicon) membrane and desalted into 10 mM $PO_4$ pH 7.4 with 25 mM NaCl, 46 mM octylglucoside on a f.p.l.c. Fast-Desalting column.

3) Hydroxyl-Apatite Resin

The hyaluronidase preparation from step 2) was combined with 10 ml of equilibrated hydroxylapatite resin (Biorad) and left on a rocker overnight at 4° C. hpHAse did not adsorb to the resin under these conditions and was recovered in the supernatant. hpHAse recovered in the supernatant was purified to homogeneity as determined by electrophoretic analysis on silver-stained 12.5% polyacrylamide gels on a Pharmacia Phast Gel System.

Table 1 is a summary of the hyaluronidase activity, protein concentration, and specific activities of the hpHAse-containing fractions during each of the purification steps described above.

TABLE 1

Biochemical Purification of hpHAse

| Purification Step | Volume (ml) | Activity (rTRU/ml) | Protein (mg/ml) | Specific Activity (rTRU/mg) | X-Fold Purification |
|---|---|---|---|---|---|
| Starting Material (human plasma) | 2,100 | 35 | 86 | 0.406 | 1.0 |
| 1) Final Detergent Phase | 650 | 33 | 1.3 | 25.4 | 63 |
| 2) Fast Flow-S Cation Exchange | 60 | 298 | 0.85 | 350.6 | 875 |
| 3) Hydroxyl-Apatite (unbound) | 15 | 907 | 0.0015 | $6.0 \times 10^5$ | $1.5 \times 10^6$ |

1) Temperature-Induced Detergent Phase Extraction

Two liters of outdated human plasma, obtained from either UCSF or Irwin Memorial blood donor centers, were routinely used for enzyme purifications. Two liters of chilled human plasma were dissolved in a solution 0.02% Sodium Azide, 50 mM NaCl, 5% sucrose and 7.5% Triton X-114 (Boehringer Mannheim) were dissolved at 4° C. with stirring for 90 min followed by centrifugation at 10,000×g for 30 min to remove insoluble material. The plasma was then subjected to temperature-induced phase extraction at 37° C. to separate the detergent-rich and detergent-poor phases. The extract was centrifuged at 10,000×g for 30 min at 37° C. to clarify the two phases. The detergent-rich phase was removed and diluted to 2 liters with cold 50 mM Hepes, pH 7.5, 0.15 M NaCl. The solution was then allowed to mix thoroughly on ice followed by repartitioning at 37° C. with centrifugation. This was repeated three times in order to increase the specific activity of the hyaluronidase that partitioned into the detergent phase. The final detergent-rich phase was enriched 60-fold for hpHAse specific activity relative to the human plasma starting material as determined by the HAse activity assay of Example 1.

Summary of Results of Biochemical hpHAse Purification

Purification of hpHAse using the biochemical method described above revealed that hpHAse has the unique property of partitioning into the temperature-induced detergent phase. hpHAse partitioning into the detergent-rich phase is usually observed with certain integral membrane or lipid-anchored proteins (Bordier 1981 *J. Biol. Chem.* 2:1604-7). Treatment of hpHAse with phosphatidylinositol specific phospholipase-C (which cleaves glycosyl-phosphatidyl inositol (GPI) anchors), phospholipase-D (which cleaves GPI anchors), or N-glycosidase-F (which cleaves N-linked glycosylated moieties) did not alter the hpHAse partitioning properties of hpHAse (although N-glycosidase-F treatment combined with gel zymography did show that hpHAse has at least two N-linked glycosylation sites).

These experiments suggested that hpHAse is an integral membrane protein or has a phospholipase-resistant anchor, similar to the GPI anchor of human erythrocyte acetylcholinesterase (Roberts et al. 1988 *J. Biol. Chem.* 263:18766-75). Although GPI anchors are normally associated with proteins that reside on the extracellular domain of the plasma membrane, there are examples of GPI anchored proteins in serum (e.g., CD59, Vakeva et al. 1994 *Immunology* 82:28-33). Furthermore, several of the neutral PH20 sperm hyaluronidases have GPI-specific phospholipase-C-susceptible anchors (Gmachl et al. 1993 *FEBS Lett.* 336:545-8; Thaler et al. 1995 *Biochemistry* 34:7788-95), but no GPI-anchor-like post-translation modifications have been described in an acid active hyaluronidases. Moreover, such post-translational modification would not be obvious from the amino acid or nucleotide sequence encoding such acid active hyaluronidases (i.e., no specific sites for post-translational modification by addition of a fatty acid or GPI anchor have been described). For example, there is no presently known consensus sequence for GPI-anchored proteins. The consensus sequence for isoprenylated proteins (CAAX) (SEQ ID NO:9) is known; however, hpHAse does not contain this sequence.

hpHAse displayed other strongly amphiphilic characteristics. For example, hpHAse precipitated from solution when the ionic strength of the solution in which hpHAse was dissolved was lowered through dialysis. hpHAse was enriched within the 0-30% ammonium sulfate fraction. The concavalin-A binding properties of hpHAse revealed that hpHAse is a mannose-containing glycoprotein.

Gel filtration chromatography on an S200-f.p.l.c. column (Pharmacia) at neutral pH resulted in elution of the HAse activity peak within the void volume at approximately 120 kDa. When gel filtration chromatography was performed in the absence of non-ionic detergents, the HAse activity peak eluted at approximately 60 kDa. This difference in the molecular weight associated with the hpHAse activity is likely due to hpHAse aggregation or oligimerzation (e.g., through intramolecular bonds) in the presence of detergents. hpHAse is very stable at 37° C. in the presence of non-ionic detergents; thus, Triton X-114 phase extractions are ideal as an initial fractionation step, particularly since few plasma proteins partition into the detergent-rich phase.

During cation exchange chromatography to remove detergent and further purify hpHAse, it was found that the addition of non-ionic detergents and maintenance of at least 50 mM NaCl was essential to prevent precipitation of the enzyme. Batch adsorption chromatography preserved activity in comparison to column chromatography. Interestingly, hpHAse activity was not retained when concentrating hpHAse-containing preparations on 10 kDa cut off membrane in the presence of 60 mM octylglucoside; however, hpHAse activity was retained by using a 3 kDa cutoff membrane. These results suggest that the Stokes radius for hpHAse deviates substantially from a spherical model. These data show that hpHAse does not have a spherical shape in the presence of octyl glucoside detergent as assumed for most globular proteins, but rather likely has more rod-like shape. hpHAse in one dimension appears to have a molecular weight of 6-7 kDa protein rather than a 57 kDa protein. The protein can thus in one dimension pass through barriers reserved to small proteins and peptides, which would explain the finding of the plasma enzyme in human urine (see infra, usually the kidney excludes proteins <50-60 kDa). Thus, patients may excrete a significant amount of hpHAse into their urine if hpHAse is not incorporated into liposome or liposome-like structures.

The post SP-Sepharose preparation of hpHAse was purified to homogeneity through adsorbtion of contaminating proteins with hydroxyl apatite resin, resulting in an overall purification of 1.5 million fold. SDS-PAGE electrophoresis and silver staining of an hpHAse sample from this final purification step revealed a single band, thus indicating that hpHAse had been purified to electrophoretic homogeneity. The specific activity of the purified enzyme (600,000 rTRU/ mg as tested using the assay described in Example 1) was roughly 6-fold that of the reported values for the sperm hyaluronidase, PH20. The purified enzyme migrated on SDS electrophoresis gels with a relative molecular mass of 57 kDa, though levels of nonionic detergents in the final preparation made molecular mass analysis variable.

Example 3

Screening Assay for Anti-Native Acid Active HAse (aaHAse) Antibodies

Biotinylated HA (bHA) was prepared as described in Example 1. Approximately 5 µg of bHA/well and 1.25 µg/well of goat anti-mouse IgG (Jackson Immunolabs) were covalently coupled to Covalink-NH microtiter plates (NUNC, Placerville, N.J.) with 9.2 µg/well Sulfo-NES (Pierce) and 6 µg/well fresh EDC overnight at 4° C. Unbound HA and goat antibody were removed through washing plates with wash buffer (PBS with 2M NaCl, 50 mM MgSO$_4$, 0.05% Tween-20).

Anti-native acid active HAse (anti-native aaHAse) antibodies were screened by incubating candidate antibodies with a sample containing an acid active HAse in a neutral pH buffer composed of 1% Triton X-100 in phosphate-buffered saline (PBS). If the sample was a diluted sample (e.g., a diluted plasma sample), the neutral pH buffer additionally contained 5 mg/ml bovine serum albumin (BSA). The aaHAse-containing sample was incubated with the candidate antibodies to allow for formation of native aaHAse-antibody complexes. The sample was then placed into bHA/anti-mouse antibody wells and incubated to allow for formation of anti-mouse antibody/anti-native aaHAse/aaHAse antibodies in the neutral pH buffer. A sample containing antibodies that do not bind aaHAse can be used as a negative control.

Detection of antibodies bound to native aaHAse was accomplished by first washing away unbound material with neutral pH buffer, then replacing the neutral pH buffer with the acidic assay buffer used in the HAse activity assay described in Example 1 (0.1 M Formate pH 3.7, 0.1 M NaCl, 1% Triton X-100, 0.02% Azide, 5 mM CaCl2 and 5 mM sacharrolactone). The shift in the pH from neutral to acidic allows for the HAse activity of any bound aaHAse to degrade the covalently bound bHA. The reaction was terminated by addition of 6 M guanidine HCL and washed three times with PBS wash buffer (PBS, 2 M NaCl, 50 mM MgSO$_4$, 0.05% Tween-20). Degradation of bHA was detected by reaction of the wells with avidin peroxidase using o-phenylendiamine as a substrate and reading the plates at 492 nm as described in Example 1. Anti-native aaHAse antibodies were identified by degradation of bHA. The assay takes advantage of the aaHAse characteristic that aaHAses have no affinity for the HA substrate above pH 4.5 (as determined through HA-Sepharose affinity chromatography with hpHAse, data not shown).

Example 4

Generation and Identification of Anti-hpHAse Monoclonal Antibodies hpHAse isolated from the post-hydroxyl apatite step in the purification method of Example 2 was used to immunize five 6 week old female Balb-c mice according to methods well known in the art (see, e.g., Harlow and Lane, supra). Briefly, the hpHAse was combined with Freund's complete adjuvant and injected intraperitoneally into the mice. At 21 day intervals, the animals were boosted with protein plus Freund's incomplete adjuvant. The fourth and final boost contained hpHAse in Freund's incomplete adjuvant was injected intravenously. Serum samples were obtained, the mice sacrificed, and spleen cells from two of the five isolated for preparation of hybridoma cell lines according to methods well known in the art (see, e.g., Harlow and Lane, supra; Schrier et al. supra). Fusion of the balb/c cells was performed with sp2/0 myelomas.

Antibody-secreting hybridomas were screened using the anti-native aaHAse antibody assay of the invention as described Example 3. Briefly, hybridoma supernatants from 20 fusion plates were incubated with diluted human plasma for 60 min at 37° C. followed by incubation in the bHA/anti-mouse-IgG plates for 60 min at 37° C. The plates were washed five times with PBS containing 1% Triton X-100 and 10 mg/ml BSA to remove non-immunoprecipitated hyaluronidase. The acidic formate assay buffer (pH 3.7) was then added to the wells and incubated at 37° C. for 60 min. After stopping the reaction with 6 M guanidine, undegraded bHA remaining in the wells was detected by reaction of the wells with avidin peroxidase using o-phenylendiamine as a substrate and reading the plates at 492 nm as described in Example 3.

Eight clones were identified from the original 20 hybridoma fusion plates. Two clones, 17E9 (producing $IgG_{2\alpha}$ class antibody; kappa chain) and 4D5 (producing $IgG_1$ class antibody; kappa chain), were used to generate ascites. Immunoglobulin from ascites of single-cell cloned hybridoma lines were generated in Balb/c mice and purified through protein-A affinity chromatography. Neither the 17E9 or 4D5 antibodies blocked hpHAse activity. The 17E9 antibody is preferred for use in immunoaffinity purification and immunoprecipitation; the 4D5 antibody is preferred for use in immunohistochemistry.

Example 5

Figure 4:
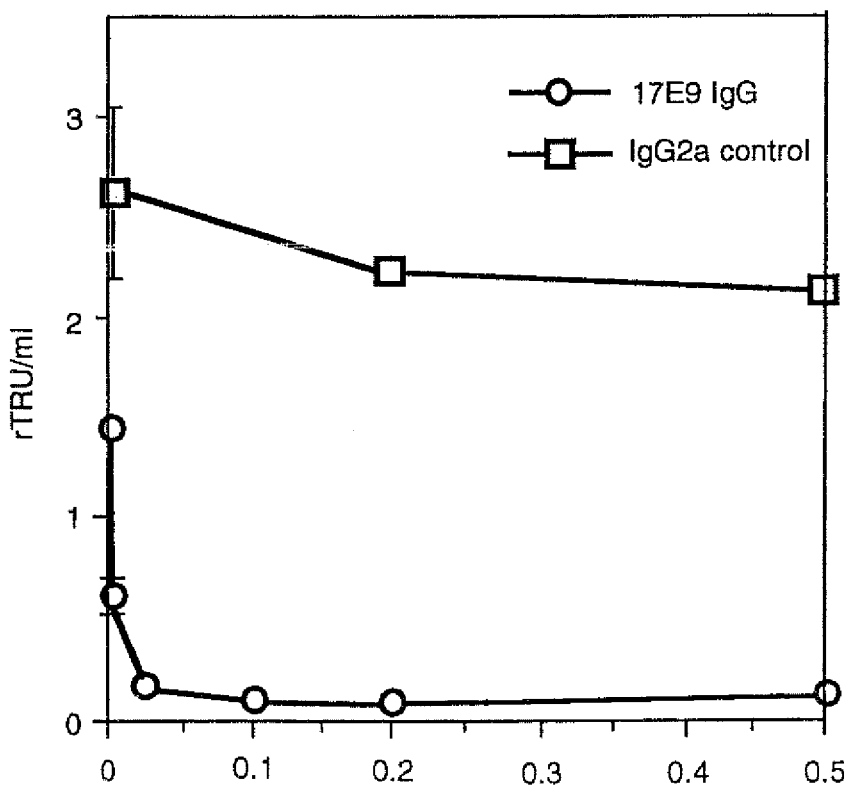
FIG. 4 is a graph showing hyaluronidase activity associated with supernatants of human plasma after immunoprecipitation with varying concentrations of anti-native hpHAse 17E9 antibody (open circles) or bound control antibody (open squares).

Immunoprecipitation of hpHAse Using the 17B9 Monoclonal Antibody hpHAse was immunoprecipitated from human plasma using either purified IgG2a from the 17E9 anti-native hpHAse clone or a control IgG2a non-specific antibody. Human plasma was diluted in R.I.P.A. buffer (1% NP40, 1% Deoxycholate, 1% Triton X-100, 5 mM EDTA in PBS). Protein-A Sepharose conjugated to serial dilutions of either control IgG2a antibody or 17E9 antibody was added to the sample. Unbound material was separated from the beads by centrifugation and the HAse activity remaining in the supernatant detected using the assay described in Example 1. As shown in FIG. 4, immunoprecipitation with the 17E9 antibody resulted in removal of essentially all of the detectable acid active hyaluronidase activity. Further, the 17E9 antibody did not bind bovine testicular hyaluronidase (PH20), suggesting that 17E9 does not bind a carbohydrate moiety or other moiety that may be shared by PH20 and hpHAse.

Example 6

Immunoaffinity Purification of hpHAse hpHAse was purified to homogeneity from raw human plasma in a single step using the 17E9 antibody bound to an immunoaffinity chromatography column. Approximately 3 mg of purified IgG from the 17E9 hybridoma clone ascites was coupled to a 1 ml High Trap-NHS activated column (Pharmacia) as per the manufacturer's instructions. Human plasma was diluted 1:2 with R.I.P.A. buffer, and passed over the 17E9 IgG antibody column. The column was then washed with PBS containing 2M NaCl, 100 mM octylglucoside followed by washing with 100 mM citrate pH 4.0. hpHAse was eluted with 100 mM citrate, pH 3.0, with 150 mM NaCl. hpHAse eluted as a sharp, homogenous peak at pH 3.0. The specific activity of immunoaffinity purified hpHAse ranged from about $4 \times 10^5$ rTRU/mg. Thus very little, if any, activity is lost in the immunoaffinity purification process relative to the biochemical purification process. Moreover, immunoaffinity purification resulted in a yield of hpHAse approximately 100% of the hpHAse in the sample; HAse assay detected no HAse activity remaining in the unbound fraction.

Example 7

Amino Acid Sequencing of hpHAse

Approximately 50 µg of immunoaffinity purified hpHAse from Example 6 was digested with Lys-C (to generate N-terminal fragments) or trypsin (to generate internal fragments) and chromatographed on a Vydac C-18 reverse phase column to separate fragments. Purified peptides were sequenced on a gas phase Edman sequencer. For N-terminal amino acid sequencing, the purified protein was immobilized on a Prosorb membrane (ABI). N-terminal amino acid sequencing was accomplished by automated protein sequence analysis using gas phase Edman degradation. Fasta queries (Pearson et al. 1988 *Proc. Natl. Acad. Sci. USA* 85:2444-8) of N-terminal and 5 separate internal amino acid sequence derived from the Lys-C digests of purified hpHAse revealed identity with the predicted amino acid sequence of the LuCa-1 gene (GenBank accession no. u03056).

Example 8

Characterization of LuCa-1/hpHAse

As described in the Example 7 above, hpHAse is identical to LuCa-1. The LuCa-1 gene is one of a group of 17 sequences located on chromosome 3p.21.3 that display a 100% loss of heterozygosity in small cell lung carcinoma lines Dietrich et al. 1966 *Clin. Chim. Acta* 2:746-52). 3p.21 deletions spanning the region containing LuCa-1 have also been described in non-small cell lung carcinomas, mammary carcinoma, carcinoma of the prostate and head and neck carcinoma. Chromatofocusing of hpHAse on a MONO-P f.p.l.c. system provided additional data regarding the identity of hpHAse and LuCa-1. hpHAse eluted at pH 6.5, very close to the LuCa-1's calculated theoretical isoelectric point of 6.58.

Figure 5:
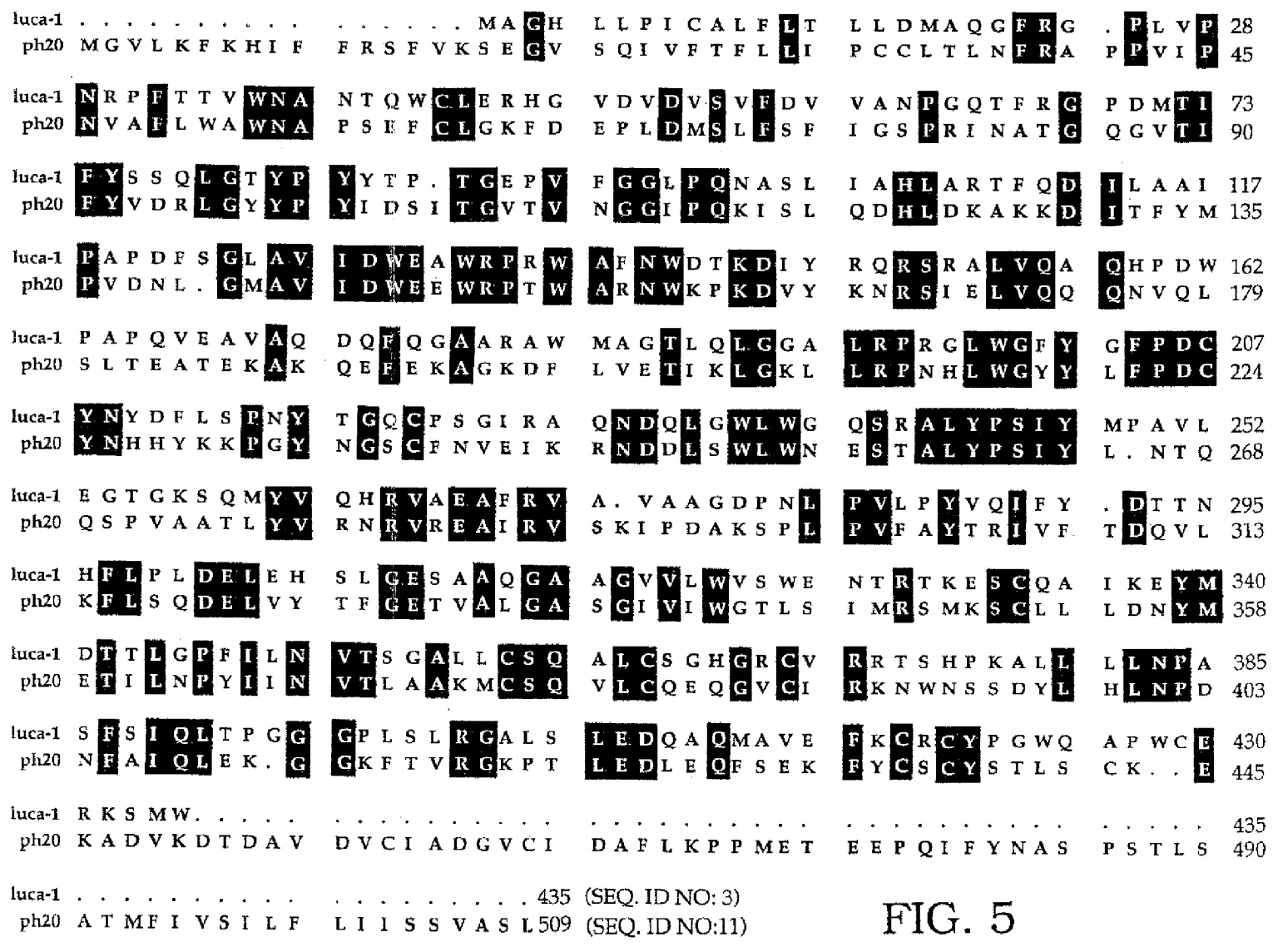

Pearson Lipman alignment (Pearson et al. supra) of LuCa-1 and human testicular hyaluronidase PH20 amino acid sequences revealed that LuCa-1 and PH20 share over 40% sequence identity and 60% percent homology (FIG. 5). PH20 is a predominantly sperm-specific neutral hyaluronidase and shares considerable homology with the venom hyaluronidases found in bee and yellow jacket vespid venoms (Gmachl et al. 1993 *Proc. Natl. Acad. Sci. USA* 90:3569-73). The striking homology between a strictly acid active plasma hyaluronidase (LuCa-1/hpHAse) and PH20 is quite surprising given their very different pH optima, suggesting that all mammalian β, 1-4 hyaluronidases, both neutral and acidic, are in members of a highly conserved family of enzymes.

Figure 6:
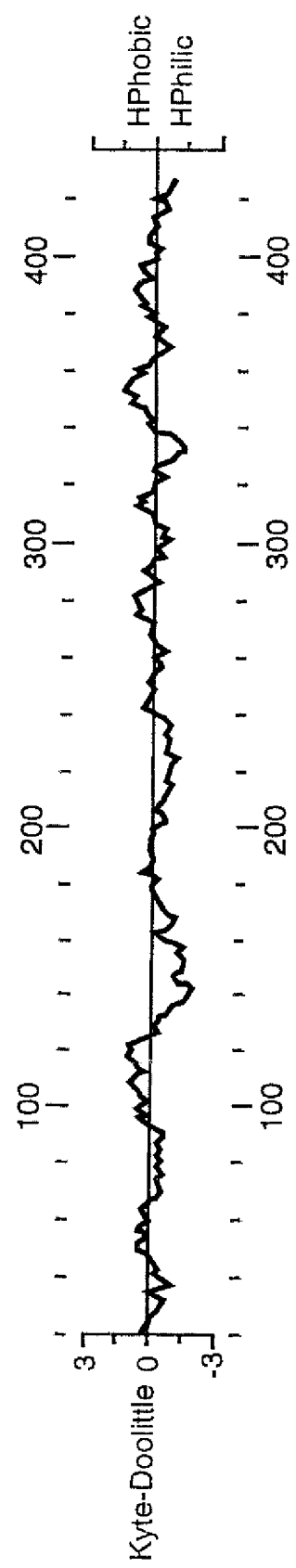
FIG. 6 is a hydropathy plot of the LuCa-1/hpHAse.

Hydropathy plots of LuCa-1/hpHAse (FIG. 6) did not reveal any rich hydrophobic domains (e.g., such as those associated with integral membrane proteins) that would explain the phase partitioning properties of hpHAse described in Example 2. These data thus suggest that partitioning of LuCa-1/hpHAse into the detergent-rich phase is due to a post-translational modification (e.g., fatty acid chain modification or phospholipase C/phospholipase D/N-glycosidase F-resistant GPI anchor.

Example 9

Isolation of LuCa-1/hpHAse-encoding DNA cDNA encoding the LuCa-1 coding sequence was isolated using two rounds of nested PCR reactions with a λgt10 5'-STRETCH PLUS Human Liver cDNA library (Clontech Laboratories, Inc., Palo Alto, Calif., USA). In the first round of PCR, which amplified nucleotides 590 to 1948 of the LuCa-1 cDNA, the following primers were used: LuCaF1 (5'-CAGGTTGTCCTGCACCAGTC-3'; SEQ ID NO:5), and LuCaR1 (5'-ATGTGCAACTCAGTGTGTGGC-3'; SEQ ID NO:6). The PCR reaction was performed in a total reaction volume of 50 ml containing 1 ml of liver cDNA library, 1 ml each of 25 mM primers, 1 ml of 10 mM dNTPs (Gibco BRL, Grand Island, N.Y., USA), 2 units of Pfu DNA polymerase (Stratagene Cloning Systems, La Jolla, Calif., USA), buffered with 10 mM Tris-HCl, 50 mM KCl, and 2 mM $MgCl_2$. The PCR reaction conditions included a 1 min denaturation step at 95° C., 1 min annealing step at 60° C., and a 1 min extension at 74° C. for 37 cycles, followed by a final 7 min extension at 74° C.

A second round of PCR amplification was used to amplify nucleotides 612 to 1925 of the Luca-1-encoding cDNA with the nested PCR primers: LuCaF2 (5'-GTGCCATGGCAG-GCCACC-3'; SEQ ID NO:7) and LuCaR2 (5'-ATCACCA-CATGCTCTTCCGC-3' SEQ ID NO:8). Primer LuCaF2 was phosphorylated prior to the PCR reaction in order to facilitate subsequent unidirectional cloning of the PCR product. Phosphorylation was carried out by incubating 2 ml of 25 mM LuCaF2 with 10 units of T4 Polynucleotide Kinase, 1 ml of 10 mM ATP buffered in 50 mM Tris-HCl pH 7.5, 10 mM $MgCl_2$, 5 mM dithiothreitol, and 0.1 mM spermidine in a final volume of 9 ml. The reaction was carried out in a total volume of 50 ml containing 1 ml of the final product from the first PCR reaction as template, 4 ml of phosphorylated LuCaF2, 1 ml of 25 mM LuCaR2, 1 ml 10 mM dNTPs (Gibco BRL), buffered with 10 mM Tris-HCl, 50 mM KCl, and 1.5 mM $MgCl_2$ and containing 0.5 units of Taq DNA polymerase (Gibco BRL). The second PCR reaction consisted of 7 cycles of a 1 min denaturation at 95° C., a 1 min annealing at 58° C., and a 1 min extension at 72° C., followed by a final extension at 72° C. for 7 min.

The product of the PCR reaction was ligated into 2 μl of the unidirectional TA-expression vector pCR3.1-Uni (Invitrogen, San Diego, Calif., USA) with T4 DNA ligase. The ligated vector was used to transform One Shot™ TOP10F' (Invitrogen) competent cells, which were plated out onto LB agar plates containing 50 μg/ml ampicillin and incubated overnight at 37° C. Colonies were tested for the presence of LuCa-1 inserts by growing overnight colonies in 10 ml LB broth with 50 μg/ml ampicillin, and by plasmid purification with the Wizard™ Plus Miniprep DNA Purification System (Promega Corporation, Madison, Wis., USA), followed by restriction mapping of the vector with Dra III endonuclease (Boehringer Manheim, Indianapolis, Ind., USA) and automated fluorescent sequencing on an ABI Prism™ DNA sequencer.

Restriction mapping with DraIII and sequencing of the plasmid showed that the cloned sequence was identical to the LuCa-1 sequence available in the GenBank database except for a $Val_{27}$-Leu substitution found in the N-terminus. Sequencing of the active PCR product from the liver λgt10 cDNA library revealed a G-C discrepancy between the sequence obtained and the published LuCa-1 sequence at the position corresponding to the 27th amino acid residue. Thus, either the published Luca-1 sequence contains an error or the clone sequenced here is an allelic variant.

Example 10

Expression of Recombinant LuCa-1 in Cos-7 Cell

The purified LuCa-1-encoding cDNA in the pCR3.1-Uni expression plasmid was transfected into 50% confluent cos-7 cells in T75 flasks for five hours using 9 μg of DNA with 60 μl of Lipofectamine in 20 ml of DME/F12 50/50 mix with non-essential amino acids (CSF cells culture facility) containing insulin, transferrin and selenium (Gibco BRL). The transfected cells were then grown for an additional 48 hr in DME/F12 50/50 mix containing 10% fetal bovine serum.

Example 11

Purification and Characterization of Recombinant LuCa-1 Expressed in Cos-7 Cells Recombinant LuCa-1 was further characterized to further verify that LuCa-1 is identical to hpHAse by virtue of its ability to bind anti-native hpHAse antibodies and exhibit acid active HAse activity. Recombinant LuCa-1 was expressed in cos-7 cells as described above and subjected to the following experiments: 1) HAse activity assays using anti-hpHAse antibodies; 2) immunoprecipitation of LuCa-1 using anti-native hpHAse antibodies; 3) gel zymography of anti-native hpHAse antibody-precipitated LuCa-1; and 4) determination of the pH optima of the acid active HAse activity associated with LuCa-1. Cells transfected with 9 μg of the pCR3.1-Uni vector containing the chloramphenicol transferase gene served as a negative control (mock-transfected cells).

Figure 7A:
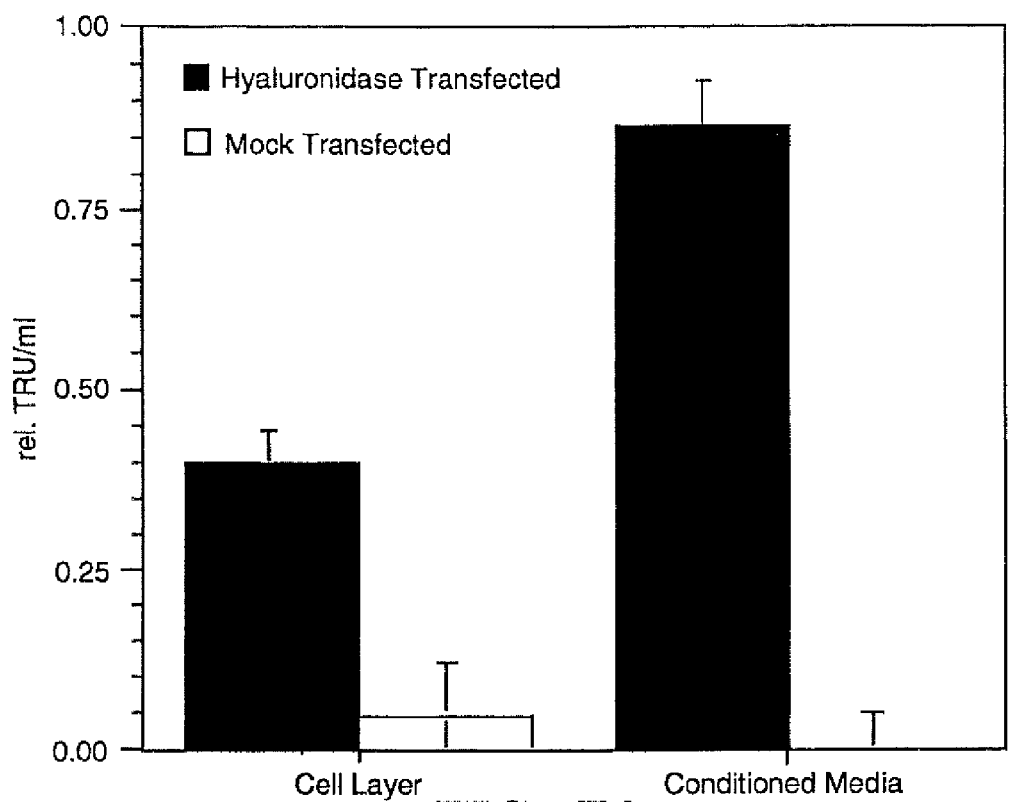
FIG. 7A is a graph showing the acid active HAse activity of detergent extracts of LuCa-1-expressing cos-7 cells and conditioned medium (shaded columns) and of mock-transfected cells and conditioned medium (unshaded columns).

HAse Activity of Recombinant LuCa-1 Using Anti-hpHAse Antibodies in the Enzyme Capture Assay Cos-7 cells expressing hpHAse and their conditioned media were separately extracted with 2% Triton X-114 followed by temperature-induced detergent phase separation as described in Example 2. The detergent-rich phase extracts were analyzed for HAse activity using the enzyme immunocapture assay of Example 1. Triton X-114 detergent phase extracts of both the cell layer and conditioned media contained an acid active HAse activity as detected in the assay of the invention (FIG. 7A). Mock-transfected control cells secreted a detectable, low-level, acid active HAse activity (FIG. 7A).

Figure 7B:
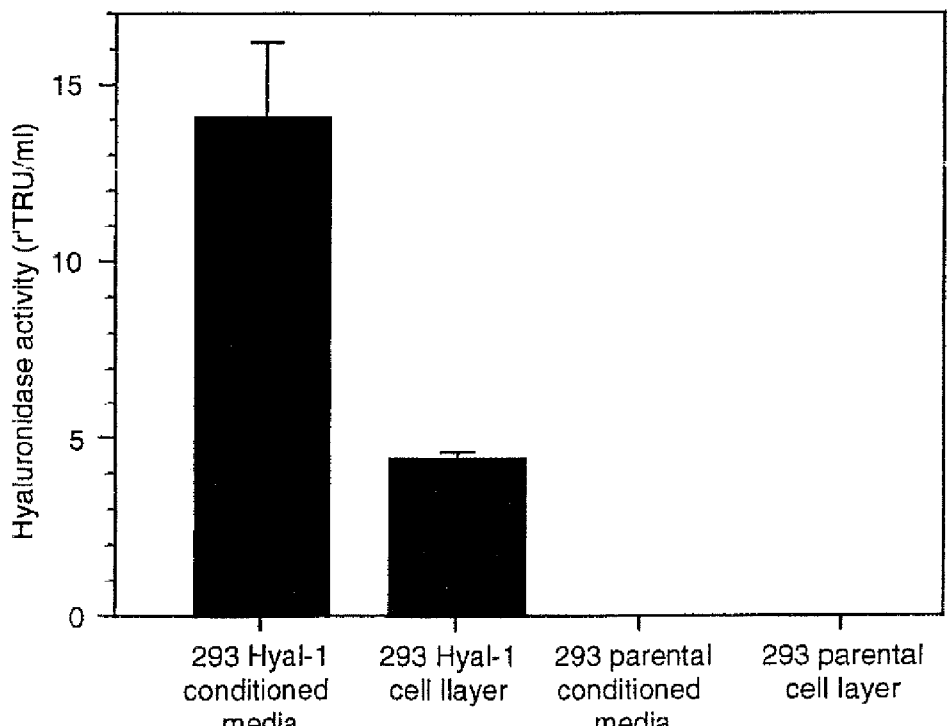
FIG. 7B is a graph showing the acid active Hase activity of detergent extracts of LuCa-1 expressing Hek 293 cells and conditioned medium (shaded columns) and of mock-transfected cells and conditioned medium (unshaded columns).

To further assess the HAse activity of recombinant hpHAse, HEK 293 cells were stably transfected with hpHAse-encoding DNA in a manner similar to that described above for transformation of Cos-7 cells. Briefly, the hpHAse-encoding construct was transfected into HEK 293 cells using 9 μg of DNA with 60 μl of Lipofectin. After 48 hrs, the cells were plated out using the limiting dilution method into 24 well plates with 500 μg/ml G418. After 14 days, the conditions media of resistant colonies was assayed for hyaluronidase activity as described above. Colonies with high level expression were expanded for further characterization. Analysis of the recombinant hpHAse was carried out by groring an HEK-293 cell line overexpressing the hpHAse-encoding construct for 48 hrs in serum free media. The condition media was passed through a 17E9 anti-hpHAse immunoaffintiy column. Recombinant hpHAse was eluted using the protocol above. As shown in FIG. 7B, both the cell layer and conditioned media contained an acid active hpHAse activity; mock-transfected cells secreted no detectable hyaluronidase activity.

These data show that LuCa-1 exhibits an acid active HAse activity, thus lending further support to the observation that hpHAse and LuCa-1 are identical.

Immunoprecipitation of Recombinant LuCa-1 with Anti-hpHAse Antibodies

Binding of anti-native hpHAse antibodies to LuCa-1 was tested in the immunoprecipitation method described in Example 5 using the 17E9 anti-hpHAse monoclonal antibody described in Example 4 bound to protein A Sepharose. The 17E9 antibodies immunoprecipitated LuCa-1 from both the LuCa-1 expressing-cells and from the conditioned media. However, the acid active HAse activity of mock transfected cells was not immunoprecipitated with the 17E9 antibody-protein A Sepharose beads. These experiments show that hpHAse and LuCa-1 share the antigenic epitope bound by the 17E9 anti-native hpHAse antibody, Moreover, this epitope is unique to hpHAse and LuCa-1, since the 17E9 did not bind an acid active HAse expressed by mock transfected cos-7 cells.

Gel Zymography of LuCa-1 Immunoprecipitated with Anti-hpHAse Antibodies

Recombinant LuCa-1 was immunoprecipitated with the 17E9 anti-native hpHAse antibody was also tested for acid active HAse activity in substrate gel zymography experiments according to methods known in the art (Afify et al. supra). Briefly, cell lysates and conditioned media from LuCa-1-transfected cells (test samples) and mock transfected cells (chloramphenicol-transferase encoding plasmid; negative control) were immunoprecipitated with anti-native hpHAse bound to protein A Sepharose beads. The samples were suspended in SDS sample buffer and electrophoresed in 10% polyacrylamide gels containing 40 µg/ml HA. Samples containing immunoprecipitated hpHAse (Example 5) and bovine testicular hyaluronidase (WYDASE™ 150 rTRU/ml) served as positive controls. Incubations were performed as described by Afify et al. (supra) and digested HA detected by staining with Alcian blue/Acetic acid followed by Commassie staining to enhance the Alcian/carbohydrate stain and visualize protein.

The region of clearing the SDS-HA gel corresponded with the same relative molecular mass as the immunoaffinity purified hpHAse preparation. No zone of clearing, and thus no immunoprecipitated acid active hyaluronidase activity was observed in the mock-transfected cell samples.

pH Optima of HAse Activity of Recombinant LuCa-1

Figure 8:
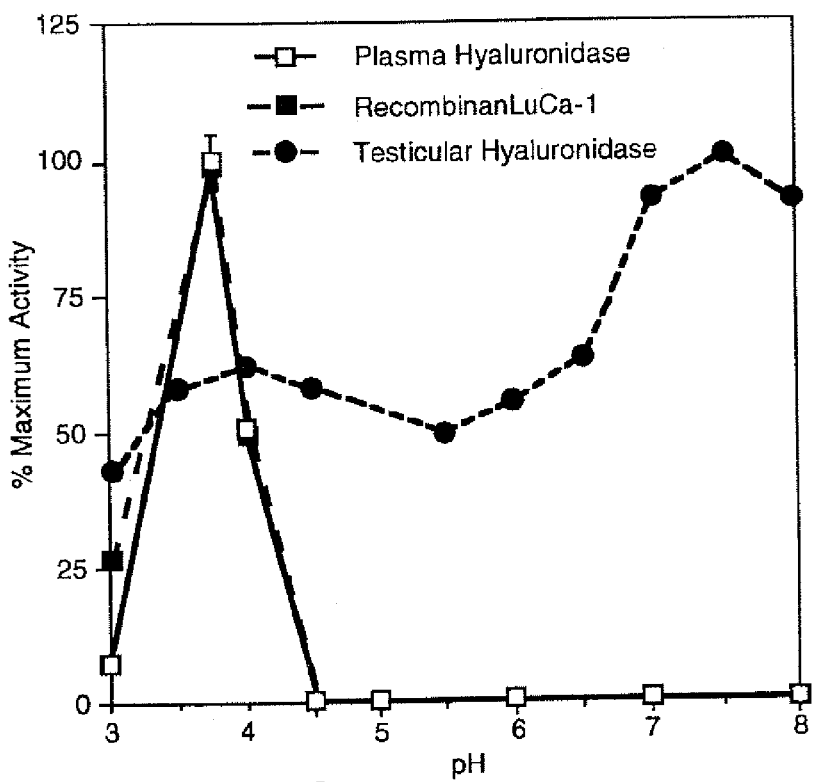
FIG. 8 is a graph showing the pH optima of the HAse activity of hpHAse purified from human plasma (open squares and solid line), recombinant LuCa-1 expressed in cos-7 cells (closed squares with dashed line), and Type VI-S testicular hyaluronidase (closed circles with dashed line).

The HAse activity assay described in Example 1 was used to determine the pH optimum of the recombinant LuCa-1 HAse activity. The HAse activity assay of Example 1 was performed as described, except that the assay buffer was composed of 0.1 M Formate pH 3-4.5, Acetate pH 5.0, Mes pH 6.0, Hepes pH 7.0-8.0, 0.1 M NaCl, 1% Triton X-100, 0.02% Azide, 5 mM CaCl2 and 5 mM sacharrolactone. Sigma Type VI-S testicular hyaluronidase (3,000 TRU/mg solid), which contains the neutral HAse PH20 (maximal HAse activity at about pH 7.5), was used as a comparison. The Type VI-S sample was treated identically, except that the assay buffer for this sample was prepared without NaCl (NaCl inhibits neutral HAse activity). As shown in FIG. 8, the pH optima curve of recombinant LuCa-1 displays the same strictly acid active profile as immunoaffinity purified hpHAse. Neither LuCa-1 nor hpHAse display HAse activity above pH 4.5; in contrast, Type VI-S testicular hyaluronidase exhibited HAse activity only above pH 7.5.

In summary, biochemical, molecular, and immunological criterion strongly indicate that LuCa-1 and hpHAse are identical.

Example 12

Organ Survey of LuCa-1/hpHAse and Transient Expression of LuCa-1/hpHAse

The primers described in Example 11 that were used to amplify the 1.3 kb coding region of the LuCa-1 cDNA were used to analyze the tissue distribution of LuCa-1/hpHAse transcripts according to methods well known in the art. Amplified PCR products from λgt10 cDNA libraries of various tissues were detected in heart, kidney, liver, lung, placenta, and skeletal muscle, but were not detected in brain. Heart tissue exhibited one of the highest levels of LuCa-1/hpHAse transcript production.

Following procedures similar to those described above, other hyaluronidases having substantially the same sequence as hpHAse of the invention can be purified, cloned, and expressed.

Example 13

Biochemical Purification of a Form of hpHAse from Urine

The urine form of hpHAse was purified from human urine according to the biochemical purification method described in Example 2, except that concentrated urine was used as the sample in lieu of outdated human plasma. Urine hpHAse partitioned into the detergent-rich Triton X-114 phase in a manner similar to that of hpHAse, suggesting the urine hpHAse contains a lipid modification similar to that of hpHAse. The isoelectric point of urine hpHAse is 6.5 as determined by elution in chromatofocusing on Mono-P f.p.l.c. Human urine hpHAse immunoprecipitated with the anti-native hpHAse antibody 17E9.

Gel zymography revealed two bands of HAse activity in crude plasma and urine samples. In plasma, HAse activity was detected in two bands corresponding to 57 kDa and 46-47 kDa; the 57 kDa band was the predominant species. In urine, HAse activity was also detected in two bands corresponding 57 kDa and 46-47 kDa; however, neither species was predominant (i.e., the bands appeared in the urine sample with equal intensity). These data suggest that hpHAse and urine hpHAse are present in plasma and urine, respectively, in two distinct modified forms (e.g., as a holoprotein and a proteolytic or otherwise modified fragment), or that there are two distinct acid active HAse proteins present in urine and in plasma.

Example 14

Expression of hpHAse in Metastasis-Derived Carcinomas

Several carcinoma lines (SCC 10A, SCC 10B, HSC-3, NIC H740, and DMS 153) were examined for the production of human plasma hyaluronidase by characterizing the levels of 17E9 immunoreactive hpHAse activity using the immmuno-precipitation assay described in Example 5 above. hpHAse levels were examined in both the conditioned media and in the cell layer itself. Normal foreskin human keratinocytes served as a positive control. The SCC 10 A cell line is derived from a primary tumor of a laryngeal carcinoma; the SCC 10B cell line is from a lymph node metastasis from the same patient. The HSC-3 cell line is derived from a lymph node metastasis. The NIC H740 cell line is a small cell lung carcinoma containing a homozygous deletion of the region of chromosome 3p21.3 encoding hpHAse. The DMS 153 cell line is a classic small lung cell carcinoma cell line (as opposed to a small lung cell carcinoma variant cell line).

Figure 9:
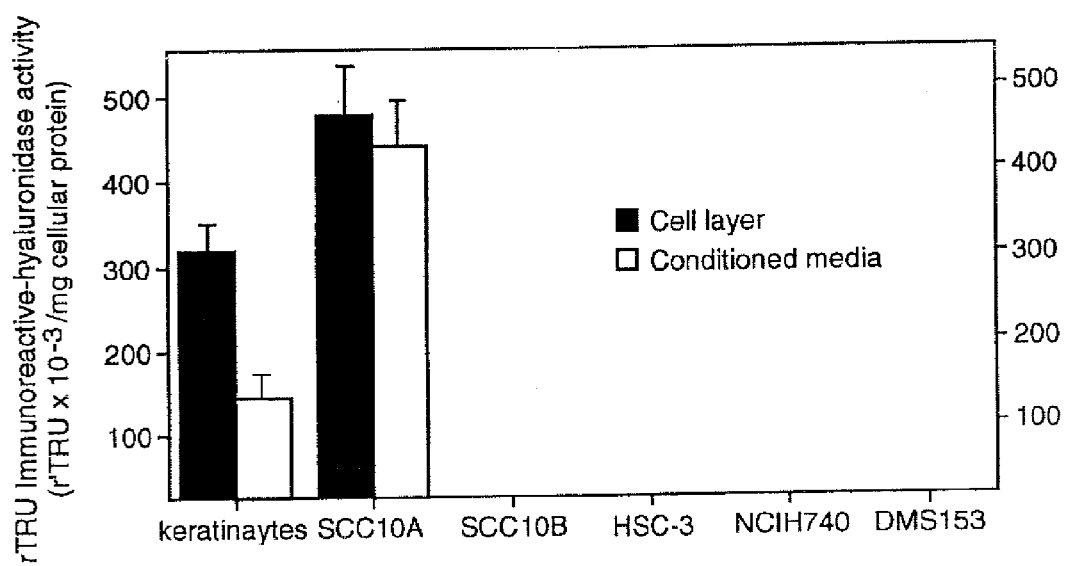
FIG. 9 is a graph showing hpHAse expression in the cell layer and conditioned media of normal human keratinocytes and several carcinoma cell lines.

As shown in FIG. 9, the SCC 10A cell lines produces hpHAse activity levels comparable to that of normal human keratinocytes, but the levels of activity in the lymph node metastasis from the same patient (SCC 10B) is completely absent in the cell layer or conditioned media. The HC-3 derived cell line exhibited no detectable hpHAse activity (the hpHAse activity assay used can accurately detect at least $\frac{1}{100}$th of the activity found in normal keratinocytes). Neither of the small cell lung carcinoma lines MNC H740 or DMS 153 have detectable activity. NIC H740 and DMS 153 cells also did not generate any detectable hpHAse-encoding transcripts (data not shown). These data suggest that loss of hpHAse expression is strongly correlated with tumorigenesis. The present inventors have identified no metastasis-derived carcinoma that produces a functional plasma hyaluronidase gene product. Some non-metastatic lines derived from primary carcinomas do have functional activity, suggesting that complete loss of enzyme function is associated with tumor metastasis.

Example 14

Recombinant hpHAse Expression System Having Improved Yield

A recombinant hpHAse expression system to provide high yields of hpHAse in the culture supernatant was developed. hpHAse-encoding DNA was operably inserted into the CMV-promoter driven PCR3.1 Uni vector (Invitrogen). This hpHAse-encoding construct was then used to transform HEK cells according to methods well known in the art. The HEK cells were then grown in a T225 $cm^2$ flask at 37° C., 5% $CO_2$ in DME H21 (4.5 g/l glucose), 10% FBS media. Conditioned culture media was collected from the cells and the levels of hpHAse assessed.

While there are often inherent difficulties generating recombinant plasma products with competitive yields to raw plasma, the recombinant hpHAse expression system described herein produces over 30-fold the amount of hyaluronidase present in raw human plasma Cohn fraction-I paste (prepared by cold alcohol precipitation according to methods well known in the art) (Table 1). In comparison, transient expression of hpHAse in Cos-7 cells expressed about 10% of the levels achieved with HEK cells. Without being held to theory, mammalian cell lines that are adenovirus transformed

TABLE 1

Levels of hpHAse in various preparations

| Enzyme Source | Hyaluronidase Activity |
| --- | --- |
| Human Plasma | 3-6 rTRU/ml |
| Recombinant Plasma HA'se Conditioned Media | 150.0 rTRU/ml |

The recombinant hpHAse from the mammalian expression system is indistinguishable from the biochemically purified enzyme as determined by using several criteria. Immunoaffinity purified recombinant hpHAse migrates with the same molecular mass as biochemically purified hpHAse. The amino acid sequence of immunoaffinity purified recombinant hpHAse has the same processed N-terminus as the native plasma enzyme (FRGPLLVP; SEQ ID NO:10). Moreover, N terminal sequencing indicates that recombinant hpHAse is processed properly in our expression system. Recombinant hpHAse has a specific activity equivalent to biochemically purified hpHAse as determined by gel zymography. 10U samples of recombinant hpHAse, biochemically purified hpHAse, and the "purest" commercial preparation of testicular hyaluronidase can depolymerize 100 μg of high molecular weight HA in 10 min. In addition, recombinant hpHAse displays the same detergent-phase partitioning properties as the biochemically purified hpHAse, suggesting that the expression system facilitates the correct post-translation processing of recombinant hpHAse.

Example 15

Activity of hpHAse in Inhibition of Tumor Growth in an Animal Model

The ability of recombinant hpHAse to inhibit tumor growth was examined in the HSC-3 bead and neck squamous cell carcinoma model, an orthotopic tumor xenografts (transplanted tumors into organ/tissue of origin). Briefly, Nu/Nu mice were orthotopically implanted with $5 \times 10^6$ HSC-3 human squamous cell carcinoma cells in Matrigel into the floor of the mouth. The cells were allowed to grow for 7 days. Animals were then segregated randomly into two groups.

Figure 10:
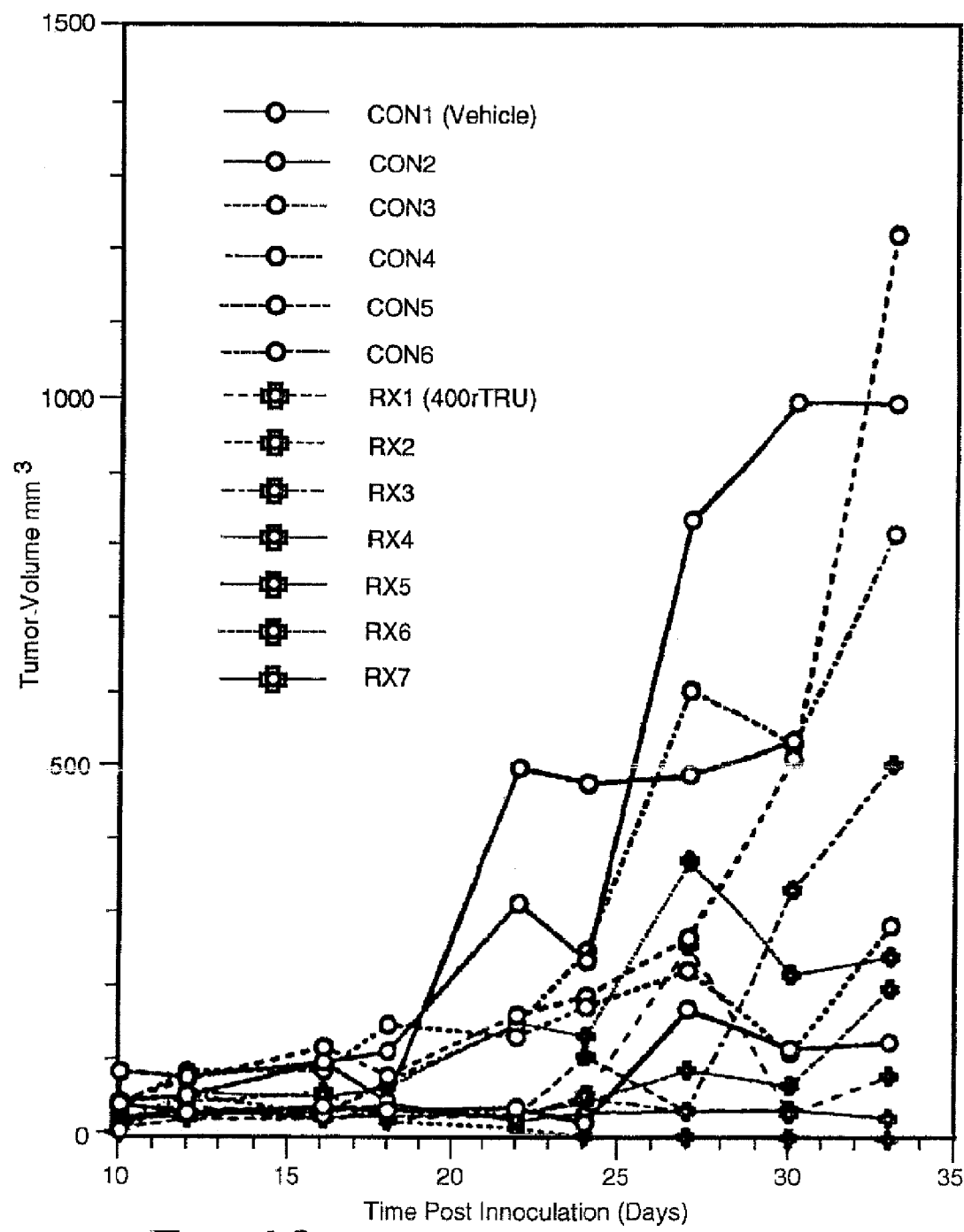
FIG. 10 is a graph showing the effects of hpHAse peritumoral injection upon growth of HSC-3 head and neck squamous cell carcinoma cells in an animal model.

Recombinant hpHASe was prepared from HEK-conditioned media overexpressing hyal-1 under a CMV promoter using an immunoaffinity column having the 17E9 IgG2a antibody coupled to NHS sepharose. Eluted hpHAse was exchanged into bovine HDL complex (Sigma) and dialyzed against Biobeads. HDL complex carrier without hpHAse served as a negative control. The material was injected into the mice peritumorally (approximately 10 mm from the primary tumor site) in a 100 μl volume. Approximately 400 rTRU hpHAse was administered per injection. Injections were repeated every 48 hours. Tumor volume was measured in 3 dimensions using a spherical model. As shown in FIG. 10, administration of hpHAse significantly reduced tumor volume.

Example 16

Inhibition of Tumor Growth by Expression of hpHAse-Encoding DNA in an Animal Model The effect of expression of hpHAse in tumor cells upon tumor growth was examined by introducing a functional hpHAse gene into a carcinoma line, where the hpHAse-encoding sequence is under control of an inducible promoter. The steroid-responsive expression plasmid ecdysone was chosen for this study since only those mammalian cells that contain the appropriate steroid-responsive plasmid responded to injection of the stimulating hormone (muristerone). This system thus permits examination of the effects of specific reactivation of the hpHAse-encoding gene within the tumor cells and assessment of in vivo effects.

HSC-3 oral squamous cell carcinoma cells were transfected with Lipofectin (Gibco) at 60 μl lipofectin, 9 μg. plasmid per T75 flask with a muristerone inducible gene construct (Ecdysone system, Invitrogen) containing the ecdysone receptor plasmid and encoding hpHAse (under inducible steroid control), as well as G418S and zeocin resistance. Cells transformed with the muristerone inducible construct without hpHAse-encoding DNA served as a control. The transformed cells were injected in the floor of the mouth of nu/nu mice at $5 \times 10^6$ cells per injection as described in Example 15. After 7 days of tumor growth, the mice received an intraperitoneal injection of muristerone (5 mg) every 72 hours to induce expression of the constructs. Tumor volumes were measured as described above in Example 15. In addition, the time to cachexia (defined by a drop in animal mass 15% below starting weight). Survival curves were generated using a Kaplan Meyer analysis using percent cachexic rather than percent surviving.

Figure 11:
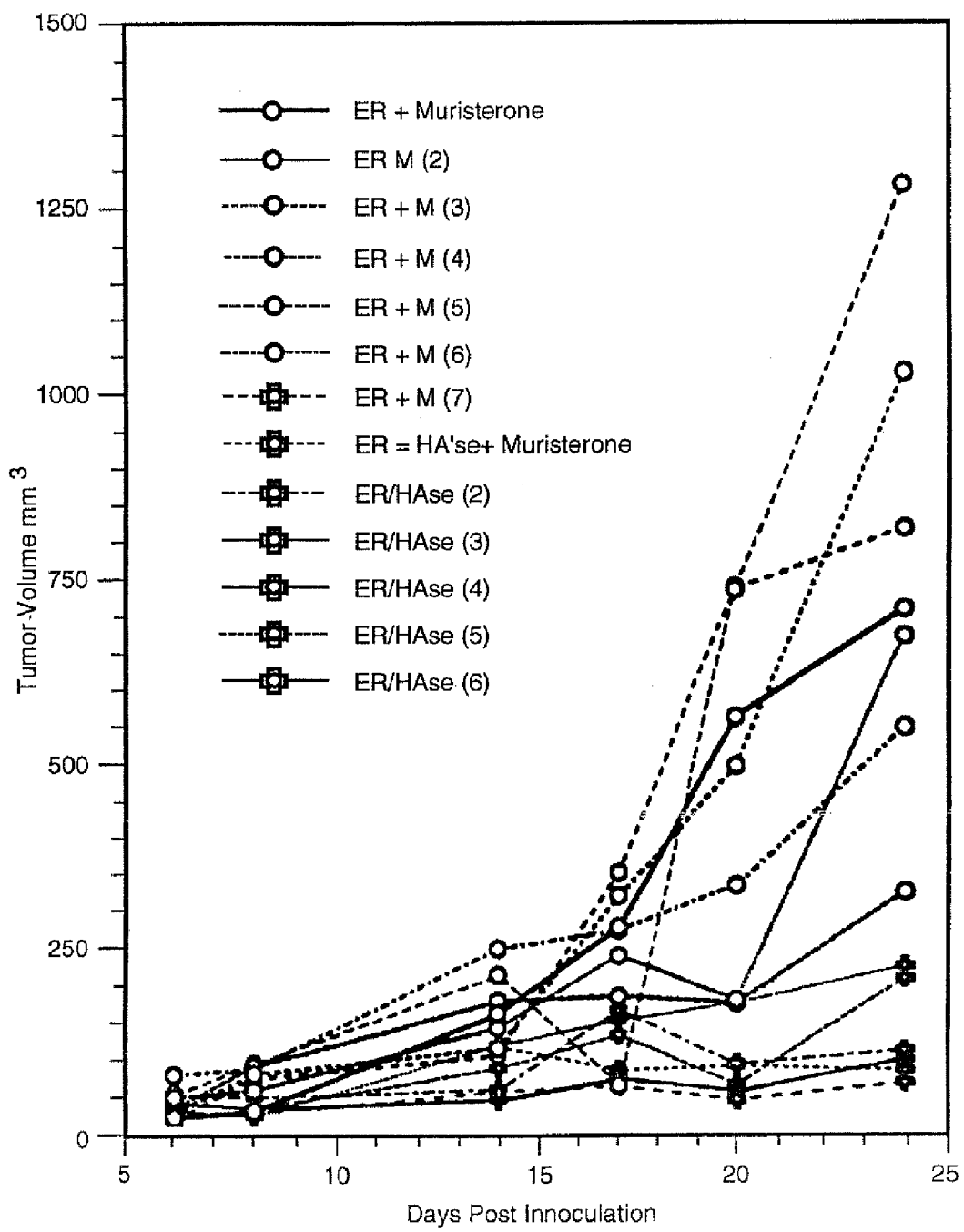
FIG. 11 is a graph showing the effects of hpHAse expression in transformed HSC-3 cells upon tumor growth in an animal model.
Figure 12:
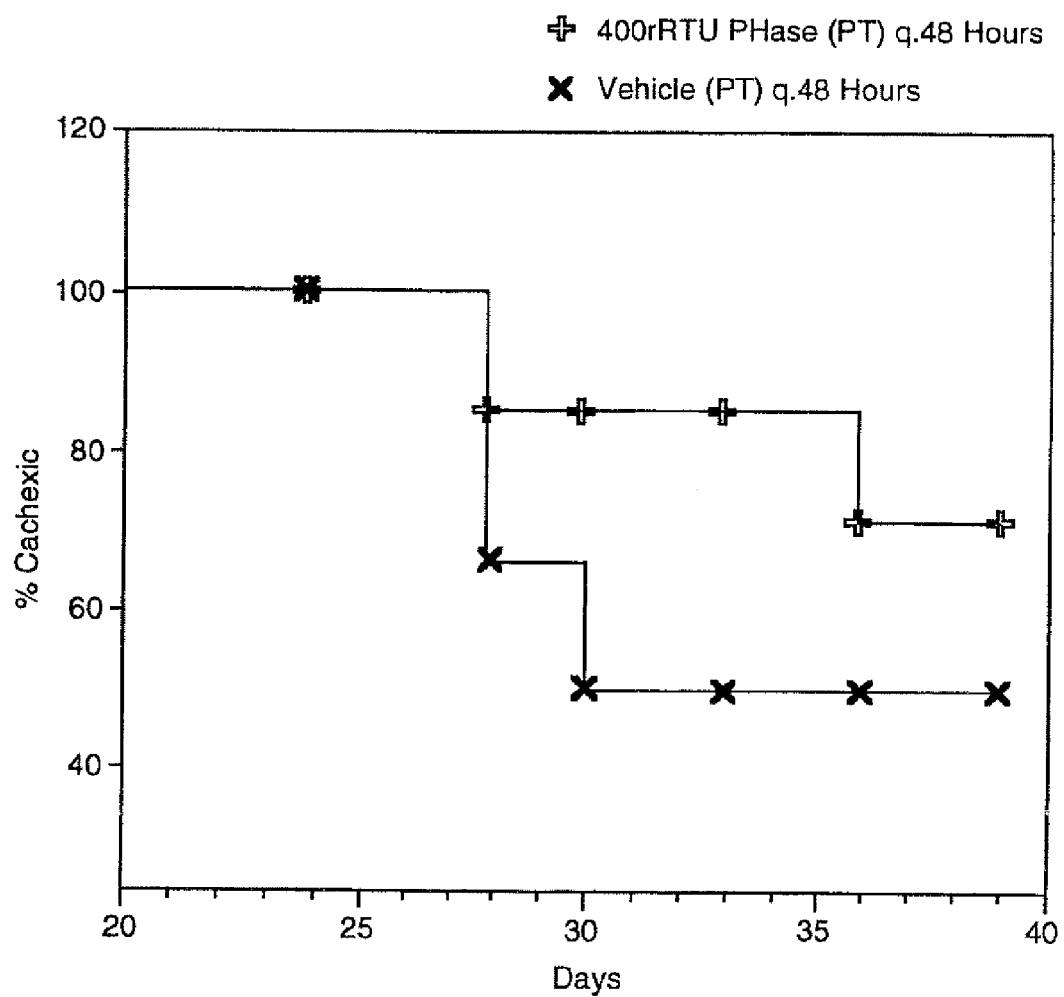
FIG. 12 is a graph showing the effects of hpHAse expression in transformed HSC-3 cells upon cachexia in an animal model.

As shown in FIG. 11, mice having HSC-3 cells transformed with the hpHAse-encoding construct were significantly reduced in tumor growth relative to control mice. Moreover, significantly fewer mice bearing the hpHAse-expressing tumor cells progressed to cachexia over the course of 39 days.

The invention now being fully described, it will be apparent to one of ordinary skill in the art that many changes and modifications can be made thereto without departing from the spirit or scope of the appended claims.

What is claimed is:

1. A method of reducing tumor growth in a patient having a type of cancer associated with a decreased level of human plasma hyaluronidase (hpHAse) activity compared to the level of human plasma hyaluronidase activity in a non-cancerous cell, the method comprising administering to the patient a substantially pure, enzymatically active, acid-active hpHAse polypeptide in an amount effective to reduce tumor growth, wherein said hpHAse has β-1,4-endoglycosidase activity in the cleavage of hyaluron, said administering resulting in reduction of tumor growth.

2. The method of claim 1, wherein said hpHAse polypeptide exhibits a specific activity from about $2 \times 10^5$ relative turbidity reducing units per mg protein to about $8 \times 10^5$ relative turbidity reducing units per mg protein.

3. The method of claim 1, wherein said hpHAse polypeptide exhibits a specific activity of about $6 \times 10^5$ relative turbidity reducing units per mg protein.

4. The method of claim 1, wherein the hpHAse polypeptide is at least 90% pure.

5. The method of claim 1, wherein the hpHAse polypeptide is at least 99% pure.

6. The method of claim 1, wherein the hpHAse polypeptide is naturally occurring hpHAse.

7. The method of claim 1, wherein the hpHAse polypeptide is recombinant hpHAse.

8. The method of claim 1, wherein the hpHAse polypeptide is formulated with a pharmaceutically acceptable carrier.

9. The method of claim 8, wherein the carrier is a liposome.

10. The method of claim 8, wherein the hpHAse polypeptide is present at a concentration of about $1.5 \times 10^5$ turbidity reducing units per milliliter of formulation.

11. The method of claim 1, wherein said cancer is metastatic.

12. The method of claim 11, wherein said administering reduces tumor metastasis.

13. The method of claim 1, wherein said cancer is selected from breast cancer, small lung cell carcinoma, brain tumor, squamous lung cell carcinoma, and head and neck carcinoma.

14. The method of claim 1, wherein said hpHAse polypeptide is administered by subcutaneous injection, intravenous injection, intramuscular injection, or peritumoral injection.

15. The method of claim 1, wherein said hpHAse polypeptide is modified to increase the serum half-life of the hpHAse polypeptide.

16. The method of claim 1, further comprising administering a cancer chemotherapeutic agent.

17. The method of claim 1, wherein said hpHAse polypeptide partitions into a non-ionic detergent-rich phase at a temperature above 25° C.

18. The method of claim 1, wherein said polypeptide is glycosylated.

19. The method of claim 18, wherein said glycosylated polypeptide is sensitive to N-glycosidase-F treatment.

20. The method of claim 18, wherein said glycosylated polypeptide comprises a mannose residue.

21. The method of claim 1, wherein said polypeptide has a relative molecular mass of about 57 kDa as determined by sodium dodecyl sulfate polyacrylamide gel electrophoresis.

22. The method of claim 1, wherein said polypeptide is at least 75% pure.

23. The method of claim 1, wherein said polypeptide exhibits a pH optimum below pH 4.5.

24. The method of claim 1, wherein said polypeptide exhibits a pH optimum of between about pH 3.0 and about pH 4.0.

25. The method of claim 1, wherein said polypeptide exhibits a pH optimum of between about pH 3.0 and about pH 3.7.

26. The method of claim 1, wherein said polypeptide is at least 99% pure.

27. The method of claim 1, wherein said polypeptide comprises an amino acid sequence having at least about 85% amino acid sequence identity to the amino acid sequence set forth in SEQ ID NO:1.

28. The method of claim 1, wherein said polypeptide comprises an amino acid sequence having at least about 90% amino acid sequence identity to the amino acid sequence set forth in SEQ ID NO:1.

29. The method of claim 1, wherein said polypeptide comprises an amino acid sequence having at least about 95% amino acid sequence identity to the amino acid sequence set forth in SEQ ID NO:1.

* * * * *

UNITED STATES PATENT AND TRADEMARK OFFICE
CERTIFICATE OF CORRECTION

PATENT NO. : 7,781,397 B2 Page 1 of 1
APPLICATION NO. : 11/538246
DATED : August 24, 2010
INVENTOR(S) : Robert Stern It is certified that error appears in the above-identified patent and that said Letters Patent is hereby corrected as shown below:

Column 1, line 18, replace with the following revised statement:

--This invention was made with government support under grant nos. CA44768, CA58207, and GM46765, awarded by the National Institutes of Health. The government has certain rights in this invention.--

Signed and Sealed this

Fifth Day of October, 2010

David J. Kappos
*Director of the United States Patent and Trademark Office*